United States Patent
Daniell

(10) Patent No.: US 10,889,825 B2
(45) Date of Patent: Jan. 12, 2021

(54) COMPOSITIONS AND METHODS THEREOF FOR DOWN-REGULATION OF GENES FOLLOWING ORAL DELIVERY OF AN RNAI MOLECULE BIOENCAPSULATED WITHIN PLANT CELLS

(71) Applicant: THE TRUSTEES OF THE UNIVERSITY OF PENNSYLVANIA, Philadelphia, PA (US)

(72) Inventor: Henry Daniell, Media, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 120 days.

(21) Appl. No.: 15/544,554

(22) PCT Filed: Feb. 22, 2016

(86) PCT No.: PCT/US2016/018973
§ 371 (c)(1),
(2) Date: Jul. 19, 2017

(87) PCT Pub. No.: WO2016/134377
PCT Pub. Date: Aug. 25, 2016

(65) Prior Publication Data
US 2018/0002716 A1    Jan. 4, 2018

Related U.S. Application Data

(60) Provisional application No. 62/119,172, filed on Feb. 21, 2015.

(51) Int. Cl.
| | | |
|---|---|---|
| *C12N 15/82* | (2006.01) | |
| *C12N 15/113* | (2010.01) | |
| *A61K 36/28* | (2006.01) | |
| *C12N 15/11* | (2006.01) | |
| *A61K 31/713* | (2006.01) | |
| *A61K 31/7105* | (2006.01) | |
| *A61K 48/00* | (2006.01) | |
| *A23K 20/10* | (2016.01) | |
| *A23L 33/00* | (2016.01) | |
| *A23L 33/105* | (2016.01) | |
| *A61K 9/00* | (2006.01) | |
| *A61K 36/81* | (2006.01) | |

(52) U.S. Cl.
CPC .......... *C12N 15/8257* (2013.01); *A23K 20/10* (2016.05); *A23L 33/105* (2016.08); *A23L 33/30* (2016.08); *A61K 9/0053* (2013.01); *A61K 31/713* (2013.01); *A61K 31/7105* (2013.01); *A61K 36/28* (2013.01); *A61K 36/81* (2013.01); *A61K 48/00* (2013.01); *C12N 15/111* (2013.01); *C12N 15/113* (2013.01); *C12N 15/8209* (2013.01); *C12N 15/8218* (2013.01); *A23V 2002/00* (2013.01); *C12N 2310/14* (2013.01); *C12N 2310/141* (2013.01); *C12N 2310/531* (2013.01); *C12N 2320/32* (2013.01); *C12N 2320/50* (2013.01)

(58) Field of Classification Search
None
See application file for complete search history.

(56) References Cited

U.S. PATENT DOCUMENTS

| | | | | |
|---|---|---|---|---|
| 2008/0113351 | A1* | 5/2008 | Naito | A61K 31/713 435/6.11 |
| 2008/0189803 | A1* | 8/2008 | Daniell | C12N 15/8214 800/278 |
| 2009/0022705 | A1 | 1/2009 | Daniell | |
| 2010/0286241 | A1 | 11/2010 | Xie et al. | |
| 2014/0007296 | A1 | 1/2014 | Huang et al. | |

FOREIGN PATENT DOCUMENTS

WO     2014106838 A2    7/2014

OTHER PUBLICATIONS

Mao et al. (Nature biotechnology 25.11 (2007): 1307). (Year: 2007).*
Thakur et al. (PloS one 9.3 (2014): e87235). (Year: 2014).*
Xue et al. (Advances in insect physiology. vol. 42. Academic Press, 2012. 73-117). (Year: 2012).*
Chan et al. (BMC bioinformatics 10.1 (2009): S33). (Year: 2009).*
Palumbo et al. (Journal of economic entomology 89.3 (1996): 735-742). (Year: 1996).*
Admyre, Charlotte et al., "Exosomes with Immune Modulatory Features Are Present in Human Breast Milk", J. Immunol., 179: 1969-1978 (2007).
Alvarez-Erviti, Lydia et al., "Delivery of siRNA to the mouse brain by systemic injection of targeted exosomes", Nature Biotechnology, 29(4): 341-345 (2011).
Aoudi, Myriam et al., "Orally delivered siRNA targeting macrophage Map4k4 suppresses systemic inflammation", Nature, 458(7242): 1180-1184 (2009).
Ballarin-Gonzalez, Borja et al., "Protection and Systemic Translocation of siRNA Following Oral Administration of Chitosan/siRNA Nanoparticles", Molecular Therapy-Nucleic Acids 2, e76 (2013).
Bologna, Nicolas G., "Processing of plant microRNA precursors", Briefings in Functional Genomics, 12(1) 37-45 (2012).
Brown, Brian D. et al., "Exploiting and antagonizing microRNA regulation for therapeutic and experimental applications", Nature, 10: 578-585 (2009).
Brummelkamp, Thijn et al., "A System for Stable Expression of Short Interfering RNAs in Mammalian Cells", Science, 296: 550-553 (2002).

(Continued)

*Primary Examiner* — Charles Logsdon
(74) *Attorney, Agent, or Firm* — Howson & Howson LLP; Kathleen D. Rigaut

(57) ABSTRACT

Compositions and methods for down-regulating genes through oral administration of RNAi molecule encapsulated in plant cells are provided.

13 Claims, 18 Drawing Sheets
Specification includes a Sequence Listing.

(56) References Cited

OTHER PUBLICATIONS

Dickinson, Brent et al., "Lack of detectable oral bioavailability of plant microRNAs after feeding in mice", Nature Biotechnology, 31(11): 965-967 (2013).
Duxbury, S. Mark et aL, "RNA interference: A mammalian SID-1 homologue enhances siRNA uptake and gene silencing efficacy in human cells", Biochemical and Biophysical Research Communications, 331: 459-463 (2005).
Elbashir, Sayda M., "Functional anatomy of siRNAs for mediating efficient RNAi in *Drosophila melanogaster* embryo lysate", The EMBO Journal, 20(23): 6877-6888 (2001).
Elhassan, Mohamed O. et al., "*Homosapiens* Systemic RNA Ingterference-defective-1 Transmembrane Family Member 1 (SIDT1) Protein Mediates Contact-dependent Small RNA Transfer and MicroRNA-21-driven Chemoresistance", The Journal of Biological Chemistry, 287(8): 5267-5277 (2012).
Fabbri, Muller et al., "MicroRNAs bind to Toll-like receptors to induce prometastatic inflammatory response", PNAS, E2110-E2116 (2012).
Flores-Jasso, C. Fabian et al., "Rapid and specific purification of Argonaute-small RNA complexes from crude cell lysates", RNA, 19: 271-279 (2013).
Garcia-Segura, Laura et al., "The Emerging Role of MicroRNAs in the Regulation of Gene Expression by Nutrients", J. Nutrigenet Nutrigenomics, 6: 16-31 (2013).
Hata, Taketoshi et al., "Isolation of bovine milk-derived microvesicles carrying mRNAs and microRNAs", Biochemical and Biophysical Research Communications, 396: 528-533 (2010).
Hirschi, Kendal D., "New foods for thought", Trends in Plant Science, 17(3): 123-125 (2012).
Hoy, Anna M. et al., "Extracellular small RNAs: what, where, why?", Biochemical Society Translations: 40(4): 886-890 (2012).
Jackson, Aimee L. et al., "Recognizing and avoiding siRNA off-target effects for target identification and therapeutic application", Nature Reviews Drug Discovery, 9: 57-67 (2010).
Jarver, Peter et al., "Peptide-mediated Cell and In Vivo Delivery of Antisense Oligonucleotides and siRNA", Molecular Therapy-Nucleic Acids: 1: e27 (2011).
Jiang, Mengxi et al., "Beyond nutrients: Food-derived microRNAs provide cross-kingdom regulation", Bioessays, 34: 280-284 (2012).
Joh, Lawrence et al. "High-Level Transient Expression of Recombinant Protein in Lettuce", Biotechnology and Bioengineering, 91(7): 861-871 (2005).
Kosaka et al., "microRNA as a new immune-regulatory agent in breast milk", Silence, 1: 7 (2010).
Liang, GaoFeng et al., "Assessing the survival of exogenous plant microRNA in mice", Food Science & Nutrition, 2(4): 380-388 (2014).
Liu, Y-N. et al., "MiR-1 and miR-200 inhibit EMT via Slug-dependent and tumorigenesis via Slug-independent mechanisms", Oncogene, 32: 296-306 (2013).
Ma, J. et al, "MicroRNA and drug resistance", Cancer Gene Therapy, 17: 523-531 (2010).

Mitchell, Patrick S. et al., "Circulating microRNAs as stable blood-based markers for cancer detection", PNAS, 105 (30): 10513-10518 (2008).
O'Neill, Martin J. et al., "Intestinal delivery of non-viral gene therapeutics: physiological barriers and preclinical models", Drug Discovery Today, 16(5/6): 203-218 (2011).
Parolini, Isabella et al., "Microenvironemtnal pH is a Key Factor for Exosome Traffic in Tumor Cells", The Journal of Biological Chemistry, 284(49): 34211-34222 (2009).
Rhim, Andrew D. et al., "EMT and dissemination precede pancreatic tumor formation", Cell, 148(1-2): 349-361 (2012).
Robbins, Marjorie et al., "2'-O-methyl-modified RNAs Act as TLR7 Antagonists", Molecular Therapy, 15(9): 1663-1669 (2007).
Schopman, Nick C.T. et al., "Optimization of shRNA inhibitors by variation of the terminal loop sequence", Antiviral Research, 86: 204-211 (2010).
Schwarze, Steven R. et al., "In Vivo Protein Transduction: Delivery of a Biologically Active Protein into the Mouse", Science, 285: 1569-1572 (1999).
Shin, Joseph D. et al., "SID-1 is a dsRNA-selective dsRNA-gated channel", RNA: 17: 1057-1065 (2011).
Tosar, Juan Pablo et al., "Mining of public sequencing databases supports a non-dietary origin for putative foreign miRNAs: underestimated effects of contamination in NGS", RNA, 20: 754-757 (2014).
Vaucheret, Herve et al., "Plant Argonautes", Trends in Plant Science, 13(7): 350-358 (2008).
Wang, Kai et al., "The Complex Exogenous RNA Spectra in Human Plasma: An Interface with Human Gut Biota?", PLoS ONE, 7(12): e51009. doi:10.1371/journal.pone.0051009 (2012).
Whangbo, Jennifer S. et al., "Environmental RNA interference", Trends in Genetics, 24(6): 297-305 (2008).
Wilson, D. Scott et al., "Orally delivered thioketal-nanoparticles loaded with TNFalpha-siRNA target inflammation and inhibit gene expression in the intestines", Nat. Mater., 9(11): 923-928 (2010).
Winston, William M. et al., "Systemic RNAi in C. elegans Requires the Putative Transmembrane Protein SID-1", Science, 295: 2456-2459 (2002).
Witwer, Kenneth W., "XenomiRs and miRNA hemeostasis in health and disease", RNA Biology, 9(9): 1147-1154 (2012).
Witwer, Kenneth W et al., "Real-time quantitative PCR and droplet digital PCR for plant miRNAs in mammalian blood provide little evidence for general uptake of dietary miRNAs", RNA Biology, 10(7): 1080-1086 (2013).
Xiang, Shuanglin et al., "Short hairpin RNA-expressing bacteria elicit RNA interference in mammals", Nature Biotechnology, 24(6): 697-702 (2006).
Yu, Bin et al., "Methylation as a Crucial Step in Plant microRNA biogenesis", Science, 307(5711): 932-935 (2005).
Zhang, Jinsong et al., "MicroRNA control of epithelial-mesenchymal transition and metastasis", Cancer Metastasis Rev., 31(0): 653-662 (2012).

* cited by examiner

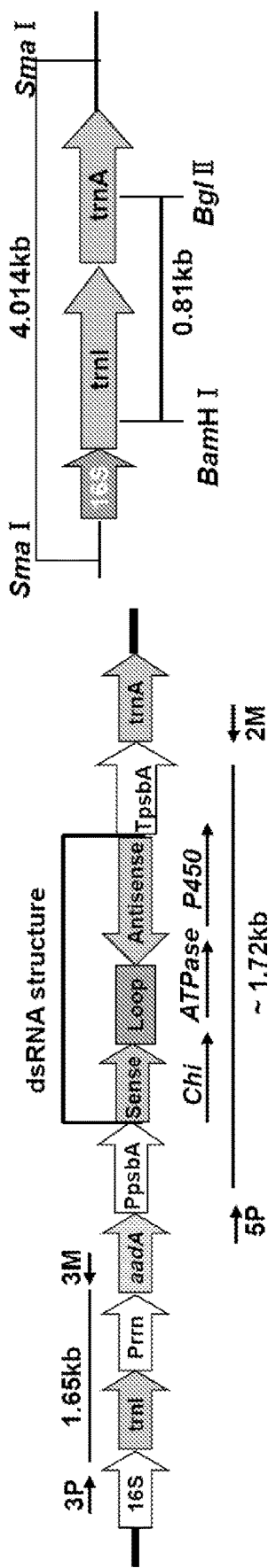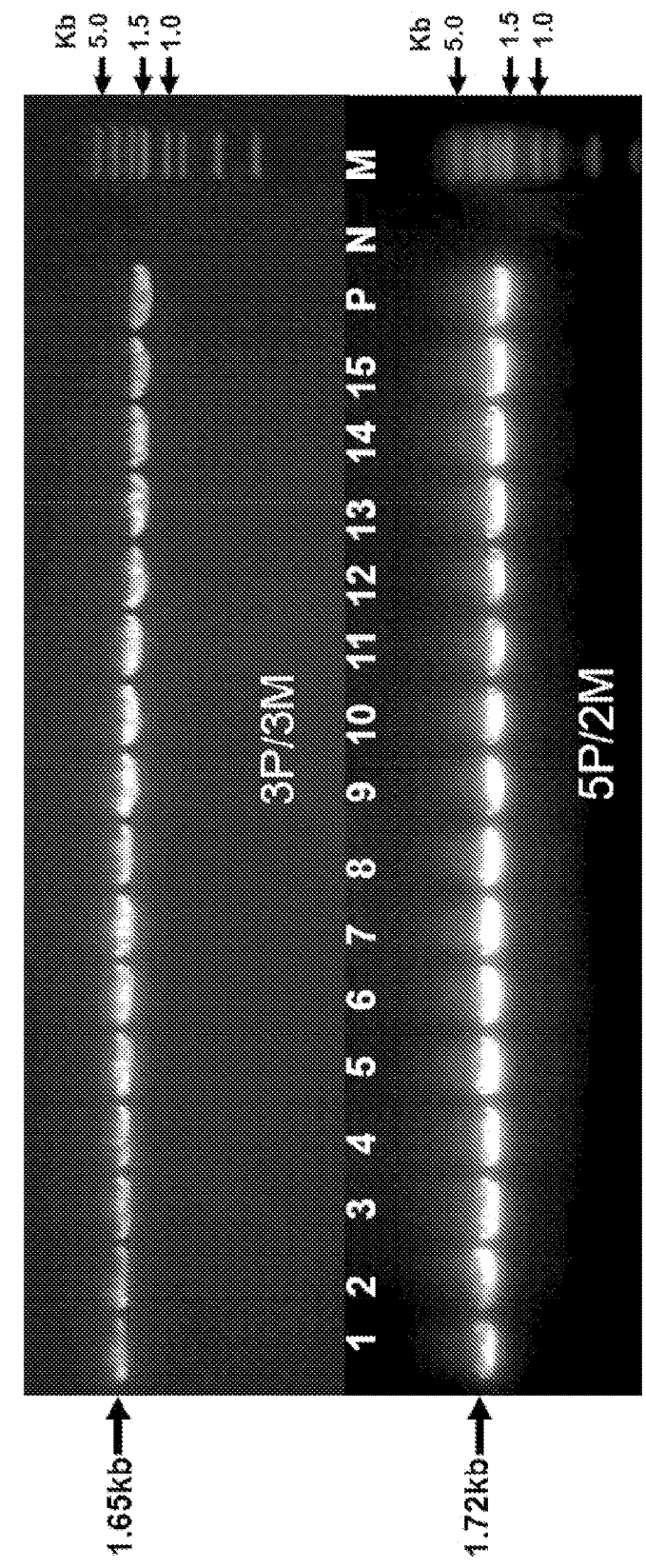
Fig. 1A
Fig. 1B
Fig. 1C

Stem-loop optimization

- UGAUAUGUGCA loop optimal with 2 matched base pairs
- ACCAAGAAG loop optimal with no matched base pairs

Increasing AT content

ATGGTGAGCAAGGGCGAGGAGCTGTTCACCGGGGTGGTGCCCATCCTGGTCGA
GCTGGACGGCGACGTAAACGGCCACAAGTTCAGCGTGTCCGGCGAGGGCGAGG
GCGATGCCACCTACGGCAAGCTGACCCTGAAGTTCATCTGCACCACCGGCAAGC
TGCCCGTGCCCTGGCCCACCCTCGTGACCACCCTGACCTACGGCGTGCAGTGCT
TCAGCCGCTACCCCGACCACATGAAGGCACGACTTCTTCAAGTCCGCCATGCCC
GAAGGCTACGTCCAGGAGCGCACCATCTTCTTCAAGGACGACGGCAACTACAA
GACCCGCGCCGAGGTGAAGTTCGAGGGCGACACCCTGGTGAACCGCATCGAGC
TGAAGGGCATCGACTTCAAGGAGGACGGCAACATCCTGGGGCACAAGCGAGTA
CAACTACAACAGCCACAACGTCTATATCATGGCCGACAAGCAGAAGAACGGCA
TCAAGGTGAACTTCAAGATCCGCCACAACATCGAGGACGGCAGCGTGCAGCTC
GCCGACCACTACCAGCAGAACACCCCCATCGGCGACGGCCCCGTGCTGCTGCCC
GACAACCACTACCTGAGCACCCAGTCCGCCCTGAGCAAAGACCCCAACGAGAA
GCGCGATCACATGGTCCTGCTGGAGTTCGTGACCGCCGCCGGGATCACTCTCGG
CATGGACGAGCTGTACAAGTCCGGACTCAGATCTCGAGCTCAAGCTTCGAATT
CTGCAGTCGACGGTACCGCGGGCCCGGGATCCACCGGATCTAGATAA

Targets contain 5' AA to generate 3' UU on guide strand

AAGCAGCACGACTTCTTCAAG – 47.6%
AAGCTGGAGTACAACTACAAC – 42.8% GC

Fig. 10

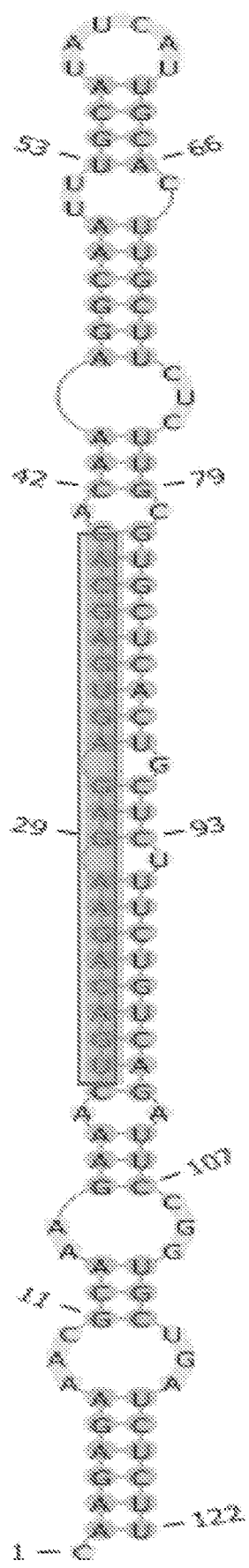
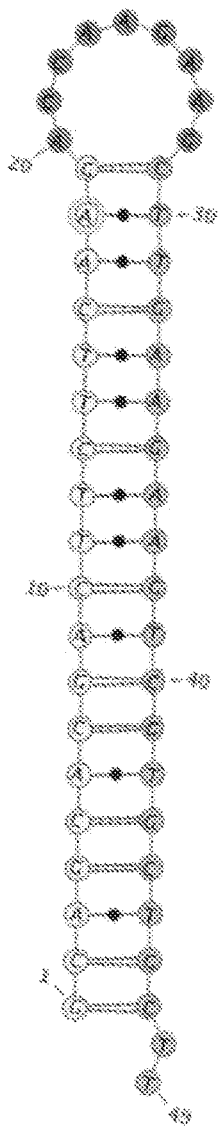
Fig. 14A
Fig. 14B

Kras G12D2 vector sequence

ASCCYTTCWTCGCTTCTTGMGAGTTCTTCTGAGCGGGACTCTGGGGTTCGGACTCTAGCTAG
AGGATCAATTCGGTACGCTGAAATCACCAGTCTCTCTCTACAAATCTATCTCTCTATTTTCTCC
ATAAATAATGTGTGAGTAGTTTCCCGATAAGGGAAATTAGGGTTCTTATAGGGTTTCGCTCATG
TGTTGAGCATATAAGAAACCCTTAGTATGTATTTGTATTTGTAAAATACTTCTATCAATAAAATTT
CTAATTCCTAAAACCAAAATCCAGTACTAAAATCCAGATCGATCCACCGCGGAACTCGACTTGC
CTTCCGCACAATACATCATTTCTTCTTAGCTTTTTTTCTTCTTCTTCGTTCATACAGTTTTTTTTG
TTTATCAGCTTACATTTTCTTGAACCGTAGCTTTCGTTTTCTTCTTTTTAACTTTCCATTCGGAGT
TTTTGTATCTTGTTTCATAGTTTGTCCCAGGATTAGAATGATTAGGCATCGAACCTTCAAGAATT
TGATTGAATAAAACATCTTCATTCTTAAGATATGAAGATAATCTTCAAAAGGCCCCTGGGAATCT
GAAAGAAGAGAAGCAGGCCCATTTATATGGGAAAGAACAATAGTATTTCTTATATAGGCCCAT
TTAAGTTGAAAACAATCTTCAAAAGTCCCACATCGCTTAGATAAGAAAACGAAGCTGAGTTTA
TATACAGCTAGAGTCGAAGTAGTGATTGTCCCTTCGGGGACATCCGATAAATTGGAATYSGTTG
GAGCTGATGGCGTAGACCAAGAAGCTACGCCATCAGCTCCAACTTTTTTTTCGAC

Fig. 16

Kras3 Vector sequence

ASCCCATCWTCGCCTTCTTGACGAGTTCTTCTGAGCGGGACTCTGGGGTTCGGACTCTAGCTAG
AGGATCATAAGTTACGCTGAAATCACCAGTCTCTCTCTACAAATCTATCtCTcTCTATTTTCTCCATAA
ATAATGTGTGAGTAGTTTCCCGATAAGGGAAATTAGGGTTCTTATAGGGTTTCGCTCATGTGTTGA
GCATATAAGAAACCCTTAGTATGTATTTGTATTTGTAAAATACTTCTATCAATAAAATTTCTAATTCCT
AAAACCAAAATCCAGTACTAAAATCCAGATCGATCCACCGCGGAACTCGACTTGCCTTCCGCACA
ATACATCATTTCTTCTTAGCTTTTTTTCTTCTTCTTCGTTCATACAGTTTTTTTTGTTTATCAGCTTA
CATTTTCTTGAACCGTAGCTTTCGTTTTCTTCTTTTTAACTTTCCATTCGGAGTTTTTGTATCTTGTT
TCATAGTTTGTCCCAGGATTAGAATGATTAGGCATCGAACCTTCAAGAATTTGATTGAATAAAACA
TCTTCATTCTTAAGATATGAAGATAATCTTCAAAAGGCCCCTGGGAATCTGAAAGAAGAGAAGCA
GGCCCATTTATATGGGAAAGAACAATAGTATTTCTTATATAGGCCCATTTAAGTTGAAAACAATCTT
CAAAAGTCCCACATCGCTTAGATAAGAAAACGAAGCTGAGTTTATATACAGCTAGAGTCGAAGTA
GTGATTGTCCCTTCGGGGACATCCGATAAAATTGGATYSGTTGGRRGCTGGTGGCGTAGCTTCTT
GGTCTACGCCACCAGCTCCAACTTTTTTTTCGACGTCCGCAAAAATCACCAGTCTCTCTCTACAAA
TCTATCTCTCTATTTTCTCCARRAATAATGKTGTGRAGTAG

Fig. 17

COMPOSITIONS AND METHODS THEREOF FOR DOWN-REGULATION OF GENES FOLLOWING ORAL DELIVERY OF AN RNAI MOLECULE BIOENCAPSULATED WITHIN PLANT CELLS

CROSS-REFERENCE TO RELATED APPLICATIONS

The present application is a § 371 of International Application No. PCT/US2016/018973, filed Feb. 22, 2016, which claims the benefit of U.S. Provisional Patent Application No. 62/119,172, filed Feb. 21, 2015. The entire disclosure of each of the aforesaid applications is incorporated by reference in the present application.

STATEMENT OF RIGHTS TO INVENTIONS MADE UNDER FEDERALLY SPONSORED RESEARCH

This invention was made with government support under grant numbers GM063879, HL109442, and HL107904 awarded by the National Institutes of Health. The government has certain rights in the invention.

FIELD OF THE INVENTION

The present invention relates to methods and compositions for down-regulating genes for conferring desired agronomic traits or for various biomedical applications, including oral delivery of RNAi effective to down-regulate dysfunctional genes associated with human disease.

BACKGROUND OF THE INVENTION

Several publications and patent documents are cited throughout the specification in order to describe the state of the art to which this invention pertains. Each of these citations is incorporated herein by reference as though set forth in full.

In the past two decades, the concept of chloroplast genetic engineering has been advanced to achieve hyper-expression of foreign proteins, with recent advances in conferring novel agronomic traits (Clarke and Daniell, 2011; Lee et al., 2011; Jin et al., 2012), biomass/biofuel enhancement (Verma et al., 2010, 2013; Agarwal et al., 2011; Jin et al., 2011) or for various biomedical applications for oral delivery of vaccines (Davoodi-Semiromi et al., 2010; Lakshmi et al., 2013; Arlen et al., 2008), autoantigens (Ruhlman et al., 2007; Verma et al., 2010; Sherman et al., 2014) or biopharmaceuticals (Kwon et al., 2013 a, c; Ruhlman et al., 2010; Boyhan and Daniell, 2010; Kohli et al., 2014; Shenoy et al., 2014; Shil et al., 2014). While application of RNAi technology through plant nuclear transformation has several limitations, delivery of small RNA prepared in more efficient systems as human therapeutics are also severely limited by their methods of delivery (Rothschild 2014). Chloroplast transformation offers several advantages over nuclear transformation including expression of large amounts of foreign proteins, up to 70% of the total leaf protein (De Cosa et al., 2001; Oey et al., 2009; Ruhlman et al., 2010). This is possible due to the polyploidy nature of the plastid genetic system with up to 10,000 copies of the chloroplast genome in each plant cell, resulting in the ability to sustain a very high number of functional gene copies (Ruiz et al., 2011). In addition, transgene containment due to maternal inheritance, lack of transgene silencing and position effect are unique advantages of chloroplast genetic engineering (Verma and Daniell, 2007; Daniell, 2007; Verma et al., 2008).

However, chloroplast has the exceptional ability to produce abundant transcripts (up to 200,000 copies per ng total RNA) but this genome has never been exploited to produce and deliver siRNA or miRNA or dsRNA. As described below, there is a great need to down regulate harmful genes to confer protection against various plant pests. In addition, down regulation of dysfunctional genes causing cancer or autoimmune diseases or immune disorders in human health is highly desired. Due to the high level of chloroplast transcription, a large amount of the dsRNA could be synthesized and orally delivered via bioencapsulation in plant cells to target harmful genes (Kwon et al., 2013c). To the best of our knowledge, there is no report on the expression the dsRNAs via the chloroplast genome modification for this purpose.

Introduction of transgenic technology in crop plants has generated insect-resistant plants to reduce yield loss and pesticide utilization (Bale et al., 2008; Kos et al., 2009). For example, expression of *Bacillus thuringiensis* (Bt) Cry toxin in crop plants has resulted in great success both economically and ecologically (Qaim and Zilberman 2003; Wu et al., 2008). However, there is emerging population of insect resistance to biopesticides in transgenic crops and outbreak of non-target pests (Bravo and Soberon, 2008; Gahan et al., 2001; Lu et al., 2010). Thus, new approaches which are more effective and environmental friendly are needed. Since the discovery of dsRNA which could silence genes (Fire et al., 1998), RNA interference (RNAi) has been developed as an efficient and powerful tool in plants and animals to silence expression of harmful genes (Wesley et al., 2001; Aravin et al., 2001). Several insect genes have been downregulated by injection of dsRNA (Bettencourt et al., 2002; Ohnishi et al., 2006). Oral delivery of high concentrations of dsRNA in the artificial diet is required (Turner et al., 2006) because they are degraded in the digestive system. Bioencapsulation within plant cells should protect dsRNA and increase their efficacy. Therefore, it is important to develop an efficient method of delivery, which could be used for large scale pest control in the field. Several dsRNA specific to target genes of insects have shown protection from these herbivores (Mao et al., 2007; Baum et al., 2007). But, advances in commercial development are limited by low abundance of siRNA transcripts.

DsRNA transgenic plant-mediated RNAi was used for silencing the hemipteran insect midgut genes and the results demonstrated the potential of dsRNA-mediated RNAi for field-level control of planthoppers (Zha et al., 2011). Viral vectors have been used to produce dsRNA in *Nicotiana attenuata* to provide a transient and rapid silencing of midgut genes of the plant's lepidopteran herbivore, *Manduca sexta* (Kumar et al., 2012). The insect resistance is significantly improved in transgenic tobacco plants expressing dsRNA from the cotton bollworm (Zhu et al., 2012). Wuriyanghan and Falk (2013) used tobacco mosaic virus (TMV) as vector to produce dsRNA in tobacco, tomato and tomatillo plants. Tomatillo plants infected with recombinant TMV containing V-ATPase or *B. cockerelli* actin sequences decreased *B. cockerelli* progeny production. Recently, Xiong et al., (2013) developed transgenic tobacco plants expressing dsRNA for a molt-regulating transcription factor gene (HaHR3) and showed increase in cotton bollworm resistance. EI-Shesheny et al., (2013) reported that silencing the abnormal wing disc gene of Asian citrus psyllid by direct application of dsRNA disrupted the adult wing development and increased the nymph mortality. It has also been shown that silencing of the HaHMG-CoA reductase gene by RNAi inhibited oviposition of the cotton bollworm (Wang et al., 2013). Despite a decade of these studies (mostly in model systems), commercial development is limited by use of viruses or prohibitively expensive application of ds RNA in the field.

Cotton bollworm Cytochrome P450 monooxygenase gene located in the midgut of insects plays a central role in adaptation of the cotton metabolite-gossypol. The RNAi target to P450 gene (CYP6AE14) has been expressed in tobacco and cotton (Hodgson et al., 1995; Mao et al., 2007, 2011). The feeding of plant cells expressing RNAi specific to Cytochrome P450 monooxygenase gene of cotton bollworm decreased transcript in the midgut, retarded larval growth and impaired cotton bollworm tolerance to the gossypol (Mao et al., 2007). Feeding of transgenic corn expressing dsRNAs target to V-ATPase gene showed a significant larval stunting and mortality (Baum et al., 2006). Pest chitin synthases (CHS) are key enzymes for trachea, cuticle and midgut development (Merzendorfer, 2006). They are encoded by CHSA and CHSB genes. CHSA genes are specifically expressed in ectodermal cells, including tracheal and epidermal cells, while CHSB genes are expressed specifically in gut epithelial cells that produce the peritrophic matrix of the midgut (Merzendorfer and Zimoch, 2003). It is well known that chitin is the main component of fungi and arthropods body skeleton, which is absent in vertebrates and plants (Zimoch et al., 2005). So, chitin synthases could be used as an ideal insect growth regulatory target for RNAi technology (Chen et al., 2008; Tian et al., 2009).

For most nuclear transformation of biopesticide genes, including those currently under commercial cultivation, the expression level is less than 1% of the total soluble protein (Ripoll et al. 2003; Saha et al., 2006). However, chloroplast transformation has resulted in much higher levels of expression and greater protection against resistant insects (Kota et al., 1999; DeCosa et al., 2001; Dufourmantel et al., 2007; Jin et al., 2011, 2012).

Since its recent discovery, siRNA has rapidly become the standard tool for gene silencing in vitro. siRNA is able to silence genes to below detectable levels with the delivery of only a small number of molecules to a cell. A well-designed siRNA can target a mutated diseased gene while sparing the wild-type counterpart, making it a highly effective therapeutic option in terms of efficacy and specificity. Billions of dollars have been spent developing a delivery mechanism for siRNA, but the major remaining hurdle is a safe and efficient delivery system. A recent seminal study demonstrated that plant miRNAs are capable of surviving the conditions of the digestive tract, entering circulation, and silencing gene expression through a plant diet. Other recent findings, such as the discovery of specific subsets of miRNA in the microvesicles of breast milk, suggest that there may be an innate pathway for uptake and processing of miRNAs through the digestive tract.

Since the 1971 National Cancer Act, billions of dollars have been invested in cancer research, yet progress in therapeutics has been relatively limited. Despite intensive efforts, cancer remains one of the leading and most devastating causes of death in the western world. Traditional chemotherapy targets dividing cells non-specifically, making the killing of cancer cells while sparing essential non-cancerous tissue a significant challenge. Newer, targeted therapies such as those using monoclonal antibodies offer a high degree of specificity, but are dependent in their action and lethality upon binding a target. Many of the most significant cancer targets are currently undruggable due to lack of extracellular targets for antibody binding or binding pockets for small molecules. There remains a great need for specific targeting of oncogenes in cancer cells.

SUMMARY OF THE INVENTION

In accordance with the present invention, recombinant plant plastid and viral expression vectors are disclosed which encode silencing RNA molecules which down modulate target genes of interest. Exemplary vectors comprise, as operably linked components in the 5' to 3' direction of translation, a promoter operable in said plant, a heterologous polynucleotide sequence coding for at least one RNAi molecule selected from the group comprising dsRNA, siRNA, shRNA, and miRNA and a transcription terminator sequences functional in said plant, wherein the vector optionally encodes a nucleic acid encoding a selectable marker. In a particularly preferred embodiment of the invention, the vector comprises a heterologous polynucleotide sequence coding for at least one RNAi molecule that down-regulates a target gene, including, without limitation, a P450 monooxygenase gene, a Vac ATPase A gene, and a chitin synthase B gene.

In yet another embodiment the heterologous polynucleotide is an RNAi molecule that down-regulates a dysfunctional gene causing or regulating cancer or immune disorders, particularly autoimmune disorders. In a particularly preferred embodiment, the RNAi down regulates K-ras and is useful for the treatment of cancer, particularly pancreatic cancer.

Transformed edible plant cells, plants derived therefrom and plant portions harvested from such plants also comprise an aspect of the invention and are useful in methods of treatment of cancer and immune disorders. Plants or plant portions within the scope of the invention, include for example, maize, lettuce, rice, grass, rye, barley, oat, wheat, soybean, peanut, grape, potato, sweet potato, pea, canola, tobacco, tomato or cotton.

In yet another aspect of the invention, a method of treating cancer or an immune disorder is provided. An exemplary method comprises oral administration to a subject an edible plant or plant portion comprising a therapeutically effective amount of an RNAi molecule expressed from a plant chloroplast selected from the group comprising dsRNA, siRNA, shRNA, and miRNA, said RNAi molecules targeting a gene which aberrantly causes or regulates the cancer or immune disorder. In a preferred embodiment of the method, the RNAi molecule down-regulates a cancer oncogene such as K-ras.

BRIEF DESCRIPTION OF THE DRAWINGS

FIG. 1A-FIG. 1F. Chloroplast dsRNA vectors, evaluation of transgene integration and homoplasmy. FIG. 1A shows the pLD-dsRNA chloroplast transformation vector map. The dsRNA structure for the target genes is the typical "sense-loop-antisense" structure. For the P450 gene, the sequence of stem-loops is shown as below: "GCAACGAGGTCGAAATGAGTTCAAGAGACTCAT-TTCGACCTCGTTGC" (SEQ ID NO: 1). For the Chi and ATPase genes, the RNAi vectors also have the similar "sense-loop-antisense" structures. The sizes of these "sense-loop-antisense" structures are ~70 nt. FIG. 1B are schematic representations of the chloroplast flanking sequences used for homologous recombination, probe DNA sequence (0.81 kb), when digested with SmaI. FIG. 1C shows a PCR analysis of the wild type and transplastomic lines using the primer pair 3P/3M (Upper) and 5P/2M (Lower). Primer annealing sites are shown in 1A. Lanes 1-5: P450:RNAi; 5-10: Chi: RNAi; 10-15 ATPase: RNAi transplastomic lines. P: positive control; N: negative control. M: DNA marker. FIG. 1D shows a Southern blot analysis of P450: RNAi transplastomic lines hybridized with chloroplast flanking sequence probe (WT, wild type and 11 transplastomic lines). FIG. 1E shows a Southern blot analysis of Chi: RNAi transplastomic lines (WT, wild type; 1-5, transplastomic lines). FIG. 1F shows a Southern blot analysis of ATPase: RNAi lines (WT, wild type; A2, A4 are negative lines; A5, B1 and B3 are heteroplasmic lines; A1, A3, A7, A8, B2, B4, A6 and C1 are homoplasmic lines.

FIG. 2A show hybridization signals of dsRNAs (FIG. 2A is unprocessed and FIG. 2B is cleaved) were detected in P450: RNAi transplastomiclines (2.3, 2.4, 2.6, 2.11 and 10.4), whereas the cleaved dsRNA product was absent in wild type plants. FIG. 2C shows hybridization signals of dsRNAs (unprocessed and cleaved) were detected in A1, A3, A6, B2, B4, B5 and B14 ATPase: RNAi transplastomic lines whereas the cleaved dsRNA product was absent in wild type. FIG. 2D are hybridization signals of dsRNAs were detected in 1-5 RNAi: Chi transplastomic lines whereas the cleaved dsRNA product was absent in wild type plants. Note: the expected dsRNAs were indicated by the arrow in FIG. 2A-C. FIG. 2E shows a transcript abundance of dsRNA in the wild type and two independent transplastomic lines-2.6 and 10.4.

FIG. 3A—In this step, most of the P450 transcripts should be degraded siRNA. FIG. 3B—Then, these larvae were transferred to the following diet or leaves: artificial diet with 3 mg/g gossypol or without gossypol; cotton leaves with glands; glandless cotton leaf and wild type tobacco leaf. In the second step, the gossypol in the artificial diet or leaves should affect larval growth and development. The weight change of larvae was measured at this step.

FIG. 4A shows a net weight increase of larvae reared on the artificial diet supplemented with gossypol (1 to 4 mg/g). The third-instar larvae were fed on the artificial diet for 5 days and then the weight increase was measured. FIG. 4B shows a net weight increase of larvae reared on artificial diet with (3 mg/g) or without gossypol, cotton leaves with or without glands and wild type tobacco leaves. Net weight increase values consist of means±standard deviation. Asterisk indicates $P<0.05$ compared with wild type control group.

FIG. 4A shows a P450 transcription level of the tested larvae fed with wild type and two transplastomic line L2.6 and L10.4 for 4 days. FIG. 4B shows a P450 transcription level of the tested larvae fed with wild type and two transplastomic lines L2.6 and L10.4 for 7 days. The primers used for quantification of dsRNAs of P450 in the transplastomic plants leaves were: upstream primer (5'-AGAGACTCATTTCGACCTCGTTGCT-3; SEQ ID NO: 6) and downstream primer (5'-GGAGCAATAGCACCCTCTT-GATAGAA-3'; SEQ ID NO: 7). The upstream primer anneals with P450 and the downstream primer anneals with TpsbA. All the results were obtained from at least three independent biological replicates. Transcription values consist of means±standard deviation. Asterisk indicates $P<0.05$ when compared with wild type control group. Two asterisks indicate $P<0.01$ when compared with wild type control group.

FIG. 6A shows a net weight increase of Helicoverpa armigera fed with ATP: RNAi transplastomic tobacco leaves for 4 days. FIG. 6B shows a net weight increase of Helicoverpa armigera fed with Chi: RNAi transplastomic tobacco leaves for 4 days; Net weight increase values consist of means±standard deviation. Asterisk indicates $P<0.05$ compared with wild type control group.

FIG. 7A shows a pupation rate of larvae fed with P450: RNAi tobacco leaves transferred to different diets or leaves. Gossypol: artificial diet containing 3 mg/g gossypol; No gossypol: artificial diet without gossypol; Glanded: glanded cotton leaves; Glandless: cotton leaves without glands; WT: wild type tobacco leaves. FIG. 7B-FIG. 7C shows a pupation rate of larvae after feeding on ATP: RNAi and Chi: RNAi tobacco leaves. FIG. 7D shows a larval mortality and pupal phenotype.1: Pupation failure led to mortality after feeding artificial diet containing 3 mg/g gossypol; 2: dead larva after feeding glanded cotton leaves; 3: dead larva after feeding with ATP: RNAi tobacco leaves; 4: dead larva after feeding with Chi: RNAi tobacco leaves; 5: successful pupation of insect fed on wild type tobacco leaves all the time during the bioassay. Pupation values consist of means±standard deviation. Asterisk indicates $P<0.05$ compared with wild type control group.

FIG. 10. Modified shRNA constructs to contain higher AT content. The sequences listed in FIG. 10, from top to bottom are reproduced as SEQ ID NOs: 21 to 23, respectively.

FIG. 14A-FIG. 14B. Design of FIG. 14A 'chimeric' structure of miR156a plant miRNA backbone with GFP targeting sequence substituted (blue box) (SEQ ID NO: 35) and FIG. 14B GFP shRNA construct (SEQ ID NO: 36).

FIG. 16: DNA sequence confirmation of the final KrasG12D2 transformation vector (SEQ ID NO: 38).

FIG. 17: DNA sequence confirmation of the final Kras transformation vector (SEQ ID NO: 39).

DETAILED DESCRIPTION OF THE INVENTION

Figure 1D:
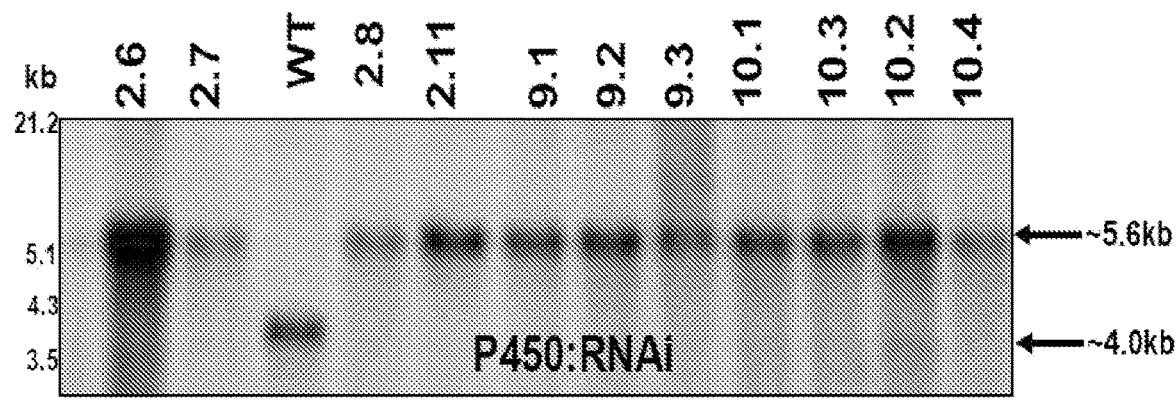

In the past two decades, chloroplast genetic engineering has been advanced to achieve high level protein accumulation but not for down-regulation of targeted genes. Therefore, in this report, lepidopteran chitin synthase (Chi), cytochrome P450 monooxygenase (P450) and V-ATPase dsRNAs were expressed via the chloroplast genome to study RNA interference (RNAi) of target genes in intended hosts. PCR and Southern blot analysis confirmed homoplasmy and site-specific integration of transgene cassettes into the chloroplast genomes. Northern blots and Real-Time qRT-PCR confirmed abundant processed and unprocessed dsRNA transcripts (up to 3.45 million copies of P450 dsRNAs/µg total RNA); the abundance of cleaved dsRNA was greater than the endogenous psbA transcript. Feeding of leaves expressing P450, Chi and V-ATPase dsRNA decreased transcription of the targeted gene to almost undetectable levels in the insect midgut, likely after further processing of dsRNA in their gut. Consequently, the net weight of larvae, growth and pupation rates were significantly reduced by chloroplast-derived dsRNAs. Taken together, successful expression of dsRNAs via the chloroplast genome for the first time opens the door to study RNA interference/processing within plastids. Most importantly, dsRNA expressed in chloroplasts can be utilized for gene inactivation to confer desired agronomic traits or for various biomedical applications, including down regulation of dysfunctional genes responsible for a variety of different medical disorders, including without limitation, cancer and autoimmune disorders, after oral delivery of dsRNA bioencapsulated within plant cells.

Oral administration is the preferred route of drug delivery due to ease of administration and patient compliance. A plant expression system would make production of drugs inexpensive and increase access of medicine to patients unable to afford current therapies. Successful delivery of RNAi would also allow targeting of currently undruggable targets such as inflammatory genes, oncogenes (ie. KRAS) and transcription factors, and could be used as a preventative measure in many diseases.

Definitions

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds.

According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the functional and novel characteristics of the sequence.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote.

An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately 1-6-fold purification of the native message. Thus, purification of at least one order of magnitude, preferably two or three orders, and more preferably four or five orders of magnitude is expressly contemplated. Thus, the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art. For instance, one common formula for calculating the stringency conditions required to achieve hybridization between nucleic acid molecules of a specified sequence homology is set forth below (Sambrook et al., Molecular Cloning, Cold Spring Harbor Laboratory (1989): Tm=81.5° C.+16.6 Log [Na+]+0.41(% G+C)−0.63 (% formamide)−600/#bp in duplex.

As an illustration of the above formula, using [Na+]= [0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C. The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated Tm of the hybrid. Wash conditions should be as stringent as possible for the degree of identity of the probe for the target. In general, wash conditions are selected to be approximately 12-20° C. below the Tm of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in I×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in O.I×SSC and 0.5% SDS at 65° C. for 15 minutes.

The term "oligonucleotide" or "oligo" as used herein means a short sequence of DNA or DNA derivatives typically 8 to 35 nucleotides in length, primers, or probes. An oligonucleotide can be derived synthetically, by cloning or by amplification. An oligo is defined as a nucleic acid molecule comprised of two or more ribo- or deoxyribonucleotides, preferably more than three. The exact size of the oligonucleotide will depend on various factors and on the particular application and use of the oligonucleotide. The term "derivative" is intended to include any of the above described variants when comprising an additional chemical moiety not normally a part of these molecules. These chemical moieties can have varying purposes including, improving solubility, absorption, biological halflife, decreasing toxicity and eliminating or decreasing undesirable side effects.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

An "siRNA" refers to a molecule involved in the RNA interference process for a sequence-specific post-transcriptional gene silencing or gene knockdown by providing small interfering RNAs (siRNAs) that has homology with the sequence of the targeted gene. Small interfering RNAs (siRNAs) can be synthesized in vitro or generated by ribonuclease III cleavage from longer dsRNA and are the mediators of sequence-specific mRNA degradation. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs may be between 15-35 nucleotides in length, and more typically about 21 nucleotides in length.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, peptide-tethering, PEG-fusion, and the like. The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of a nucleic acid molecule that encodes a dsRNA. Host cell machinery then translates mRNA into a polypeptide. Those skilled in the art will recognize that a nucleic acid vector can contain nucleic acid elements other than the promoter element and the dsRNA encoding nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like. The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism," or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, small molecules, antibodies, peptides, peptide/DNA complexes, and any nucleic acid based molecule.

In certain embodiments of the invention, the dsRNAi produced as described herein will be administered to a patient in combination with conventional chemotherapeutic agents to increase beneficial therapeutic effects. Such agents include, for example, placitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives.

The following materials and methods are provided to facilitate the practice of the present invention.

Generation and Molecular Characterization of Transplastomic Plants

Young tobacco leaves (4 weeks old) were bombarded with chloroplast dsRNA vectors using the biolistic device PDS1000/He and transplastomic lines were recovered as described previously (Jin et al., 2011). Bombarded leaves were then subjected to three rounds of selection. First two rounds of selection were performed on the regeneration medium of plants (RMOP) and the third round of selection was made on hormone free half MS medium (½ MSO) medium. Growth media were supplemented with 500 mg/L spectinomycin. After selection, putative transplastomic shoots were transferred to pots in the greenhouse to increase biomass.

Tobacco genomic DNA was isolated from the untransformed and spectinomycin-resistant transplastomic lines using DNeasy plant mini kit (Qiagen). PCR analysis was used to confirm transgene integration into the chloroplast genome using two sets of primers—3P-3M and 5P-2M as described previously (Jin et al., 2011, 2012). The 3P primer (5'-AAAACCCGTCCTCAGTTCGGATTGC-3; SEQ ID NO: 2) anneals with the native chloroplast genome and 3M primer (5'-CCGCGTTGTTTCATCAAGCCTTACG-3; SEQ ID NO: 3) anneals with the aadA gene. Therefore this pair of primers was used to check site-specific integration of the selectable marker gene into the chloroplast genome. The 5P primer (5'-CTGTAGAAGTCACCATTGTTGTGC-3; SEQ ID NO: 4) anneals with the selectable marker gene aadA and 2M primer (5'-TGACTGCCCACCTGAGAGCGGACA-3; SEQ ID NO: 5) anneals with the trnA gene, which were used to confirm integration of the transgene expression cassette.

Southern blot analysis of putative transplastomic lines was performed according to our previous protocol (Singh et al., 2009; Jin et al., 2011, 2012). In brief, total genomic DNA (~2 µg) isolated from third round of selection was digested with SmaI and separated on a 0.8% agarose gel and then transferred to a nylon membrane. The pUC-Ct vector DNA was digested with BglII and BamHI to generate a 0.81 kb fragment of the flanking sequence. The digested DNA bands were labeled with $^{32}P$ α[dCTP] and the membrane was hybridized using Stratagene QUICK-HYB hybridization solution followed by manufacturer's protocol.

Northern Hybridization, Real-Time PCR (qRT-PCR) Analysis of Small RNAs

Total RNA was isolated from fully expanded wild type and transplastomic tobacco leaves by Qiagen RNeasy Mini Kit (Qiagen) and quantified by Nanodrop.

For the northern blot, equal amount of total RNA (2 µg) was separated on 1.0% denaturing agarose gel and transferred to the nylon membrane (Nytran SPC; Whatman). The PCR amplified product from 3' psbA UTR was used as the probe for northern blot of P450:RNAi, Chi: RNAi and ATPase: RNAi transplastomic lines. Membrane was hybridized with PCR amplified DNA fragment labeled with $^{32}P$ [dCTP] using the QUICK-HYB hybridization solution following manufacturer's protocol (Stratagene).

For the Real-Time qRT-PCR, total RNA was isolated using TRIzol reagent (Invitrogen. USA). The third-instar larvae were fed on transplastomic P450: RNAi or wild type tobacco leaves for 4 days or 7 days and then the midguts of these tested insects were isolated under stereomicroscope and then washed with ddH$_2$O to remove any debris. The cleaned midgut tissues were stored in 70% ethanol at −20° C. until use. After removing the genomic DNA using DNase I, 1.0-2.0 µg of total RNA from tobacco leaves or cotton bollworm midgut tissue was reverse-transcribed to cDNA using a commercially available kit (Applied Biosystems, USA). Quantitative real-time PCR was performed with My-IQiCycler (Bio Rad, USA) using 2×SYBR Green master mixes. The primers used for quantification of dsRNAs of P450 in the transplastomic plants leaves were: upstream primer (5'-AGAGACTCATTTCGACCTCGTTGCT-3; SEQ ID NO: 6) and downstream primer (5'-GGAGCAATAGCACCCTCTTGATAGAA-3; SEQ ID NO: 7). The upstream primer anneals with P450 and the downstream primer anneals with TpsbA. Quantification was performed by the delta cycle time method with *Helicoverpa zea* β-Actin using as an internal standard for normalization. All the results were obtained from three independent biological replicates.

Insect Culture and Feeding Bioassays

Cotton bollworm (*Helicoverpa armigera*) eggs were purchased from Benzon research laboratory. See the world wide web at benzonresearch.com/insectlist.htm. They were hatched at 25° C. and all the larvae were fed with the artificial diet (Southland Products Incorporated on the world wide web at tecinfo.com/~southland/. All dishes were kept at 25° C. on a 14-h-day/10-h-night cycle. For the gossypol tolerance experiments, third instars larvae were transferred to the artificial diet supplemented with gossypol (0-4 mg) for 4 d and the increase in weight was recorded.

For the P450: RNAi bioassay, the larvae were reared on artificial diet until they developed to third-instar stage. These third instar larvae were fed with tobacco leaves expressing P450 RNAi for 3 d. Then, the larvae were transferred to the following diets or leaves: (A) artificial diet; (B) artificial diet supplemented with 1-3 mg g-1 of gossypol; (C) glanded (gossypol containing) cotton leaves; (D) glandless cotton leaves respectively for 4 days. After feeding for 4 days, the increase in weight of the larvae from these four groups was recorded. For the Chi and ATPase RNAi feeding bioassay, third-instar larvae were fed on the transplastomic leaves expressing dsRNA targeted to Chi and ATPase genes for 4 days. The increase in weight of the larvae was recorded. For each treatment, 10 larvae were used and the experiment was repeated 3 times. After different feeding experiments, all larvae were put back on the artificial diet until pupae emerged. The mortality and pupation rate were recorded at the end of these experiments.

Statistical Analysis

All statistical analyses were performed with SAS software (SAS Institute Inc.). Significance of variance was determined after the one way ANOVA ($P > 0.05$) and is presented in all graphs as mean±S.E.

The following examples are provided to illustrate certain embodiments of the invention. They are not intended to limit the invention in any way.

EXAMPLE I

Engineered Chloroplast dsRNA Silences Cytochrome P450 Monooxygenase, V-ATPase and Chitin Synthases Genes in the Insect Gut and Disrupts *Helicoverpa Armigera* Larval Development and Pupation Construction of Chloroplasts Transformation dsRNA Vectors Three target genes form *Helicoverpa armigera* were used for RNA interference (RNAi) induced through dsRNA P450 gene (P450, GenBank: DQ986461.1, CYP6AE14), Vac ATPase A gene (ATPase, GenBank: HM629434.1) and chitin synthase B gene (Chi, EST cloned from midgut RNA of *Helicoverpa armigera*). The candidate target sites of these genes were obtained by the GenScript siRNA Target Finder on the world wide web at genscript.com/siRNA_target_finder.html#. Sequences were filtered to eliminate candidates with unfavorable thermodynamic properties. Length of siRNA target site was set as 21 mers. Low GC content (<60) was maintained to enhance siRNA functionality. For each target, free energy of sense and antisense was calculated and sequences with strong internal structures were eliminated. Likewise, tandem repeats were removed. Candidates were ranked based on algorithm using AE The dsRNA structure for the target genes is the typical "sense-loop-antisense" structure. The loop structure for these dsRNA is 'TTCAAGAGA'. The sequence of stem-loops for the P450, ATPase, Chi genes are shown below and the loop sequence is indicated by underline: 5'-GCAACGAGGTCGAAAT-GAGTTCAAGAGACTCATTTCGACCTCGTTGC-3' (SEQ ID NO: 1); 5'-GTCACTGACGTAGTGCTGGTT-CAAGAGACCAGCACTACGTCAGTGAC-3(SEQ ID NO: 8)'; 5'-GGTGAGGACCGATGGCTCTTT-CAAGAGAAGAGCCATCGGTCCTCACC-3'(SEQ ID NO: 9). More details on dsRNA primers and vector construction are shown in Table 1.

TABLE 1

| DsRNA structure for RNAi cassettes and primers for dsRNA synthesis | |
|---|---|
| Target genes | dsRNA structure for the target genes (sense-<u>loop</u>-antisense) |
| Cytochrome P450 | GCAACGAGGTCGAAATGAG<u>TTCAAGA</u><br><u>GA</u>CTCATTTCGACCTCGTTGC *(1) |
| ATPase A | GTCACTGACGTAGTGCTGG<u>TTCAAGA</u><br><u>GA</u>CCAGCACTACGTCAGTGAC (8) |
| Chitin synthase B | GGTGAGGACCGATGGCTC<u>TTTCAAGA</u><br><u>GA</u>AGAGCCATCGGTCCTCACC (9) |

| Primers for dsRNA vectors construction | |
|---|---|
| Primer | Sequence (5'-3') |
| Upstream primer:<br>Pa (psbA promoter) | TTCC<u><b>GTCGA</b></u>CGTAGAGAAGTCCGTAT<br>    SalI<br>TTTTC (10) |
| Downstream primer:<br>Pb-1 (P450 dsRNA<br>for psbA poromoter) | GTCGAAATGAG<u><b>TCTCTTGAA</b></u>CTCATT<br>TCGACCTCGTTGCCAACAGTATAACA<br>TGACTTATATACTCGTGTCA (11) |
| Downstream Pb-2<br>(ATPase dsRNA<br>for psbA poromoter) | GACGTAGTGCTGG<u><b>TCTCTTGAA</b></u>CCAG<br>CACTACGTCAGTGACCAACAGTATAA<br>CATGACTTATATACTCGTGTCA (12) |

TABLE 1-continued

DsRNA structure for RNAi cassettes
and primers for dsRNA synthesis

| | |
|---|---|
| Downstream Pb-3 (chitin synthase dsRNA for psbA poromoter) | CCGATGGCTCTTCTCTTGAAAGAGCC ATCGGTCCTCACCCAACAGTATAACA TGACTTATATACTCGTGTCA (13) |
| Downstream Pc (psbA terminator) | CAGTTGACCTGCAGCCCAAACAAATA PstI CAAAATCA (14) |
| Upstream Pd-1 (P450 dsRNA for psbA terminator) | TGAGTTCAAGAGACTCATTTCGACCT CGTTGCTTTTTTTCTAGAGATCCTGG CCTAGT (15) |
| Upstream Pd-2 (ATPase dsRNA for psbA terminator) | TGGTTCAAGAGACCAGCACTACGTCA GTGACTTTTTTTCTAGAGATCCTGGC CTAGT (16) |
| Upstream Pd-3 (Chitin synthase dsRNA for psbA terminator) | TCTTTCAAGAGAAGAGCCATCGGTCC TCACCTTTTTTTCTAGAGATCCTGGC CTAGT (17) |

*numbers in parentheses are SEQ ID NOS:

The primer Pa and Pb were used to amplify the pbsA promoter and part of dsRNA sequence by PCR. Similarly, primer Pc and Pd were used to amplify part of dsRNA and the psbA terminator. Because the 3' of PCR product of Pa & Pb primers have a 23-25 bp complementary sequence with the 5' of PCR product from Pc & Pd primers, they should anneal into a dsRNA expression cassette (PpsbA::ds RNA:: TpsbA) (Table 1). Formation of such ds RNA stem loop structures is very common in chloroplast 5' UTR and 3' UTR transcripts (Zou et al., 2003; Merhige et al., 2005; Ruhlman et al., 2010). Two restriction enzyme sites (SalI & PstI) were also introduced into this dsRNA expression cassettes by PCR (Table 1). The dsRNA expression cassettes were double digested by SalI & PstI and then subcloned into the tobacco chloroplast transformation vector-pLD vector (Jin et al., 2011; Jin et al., 2012; Verma and Daniell, 2007)

The chloroplast transformation vectors were constructed based on the pLD vector (Daniell et al., 1998; 2001). In pLD-Chi: RNAi, pLD-P450: RNAi and pLD-ATPase: RNAi chloroplast vectors, the dsRNAs are regulated by the psbA promoter and its 5' and 3' untranslated regions (FIG. 1a). Spectinomycin-resistance gene (aadA) was used as the selectable marker for plant regeneration and is driven by the Prrn constitutive rRNA operon promoter with GGAG ribosome-binding site. The inverted repeat region trnI/trnA was used as flanking sequences for homologous recombination into the chloroplast genome (FIG. 1a). Generation and molecular characterization of dsRNA transplastomic lines Transplastomic plants were created as described previously (Jin et al., 2011; Verma et al., 2008). Several shoots emerged after bombardment of chloroplast vectors with gold particles coated with each pLD-RNAi plasmid in the first round of selection. The second round of selection advanced shoots towards homoplasmy and the third round of selection in root induction medium established independent transplastomic lines. After third round selection and confirmation by the PCR and Southern analysis, the transplastomic lines were moved to the greenhouse for increasing biomass and further characterization. Two sets of primers, 5P/2M and 3P/3M were used for PCR analysis to confirm site-specific integration of transgenes into the chloroplast genome. The 3P/3M primers pair annealed to the native chloroplast genome upstream of the site of integration and the aadA gene, resulting in a 1.65 kb PCR product. The 5P and 2M primers were used to confirm integration of dsRNA expression cassettes, which produced a 1.72 kb PCR product. PCR results confirmed the expected size products in all of the transplastomic lines which were absent in the wild type control plants (FIG. 1a, 1c).

Figure 1E:
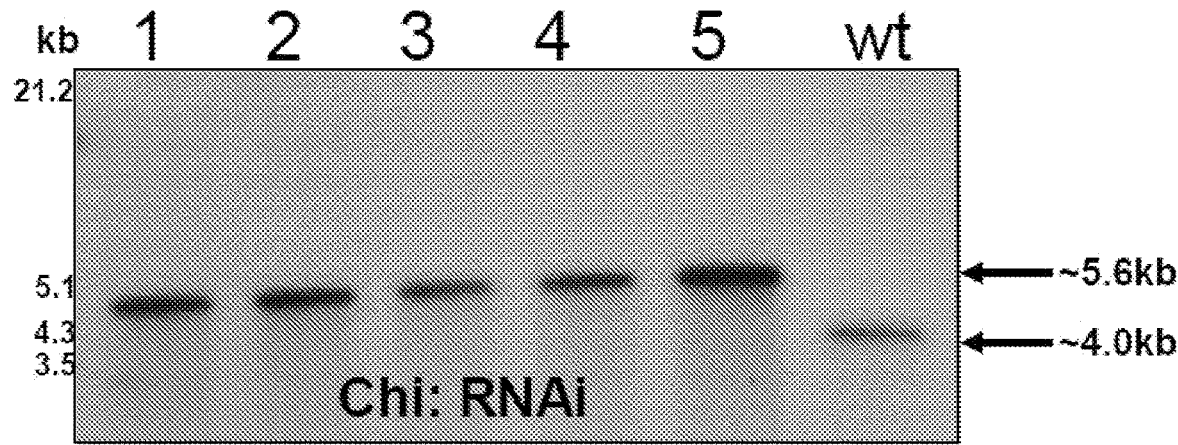
Figure 1F:
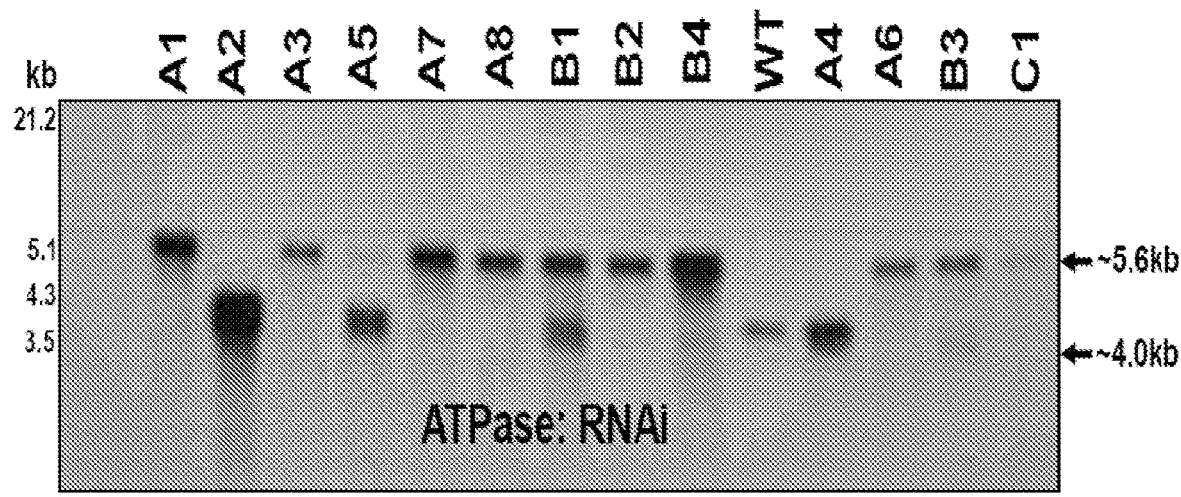

Southern blot analysis was used to determine homoplasmy and to confirm site-specific integration of transgenes into the chloroplast genome. Total plant DNA digestion with SmaI, generated 5.6 kb fragments from transplastomic lines after hybridization with the [32P]-labeled trnI-trnA flanking sequence probe. This confirmed site-specific integration of the transgenes into the spacer region between the trnI and trnA genes (FIG. 1b). Furthermore, the absence of the 4.0 kb fragments in pLD-Chi: RNAi, pLD-p450: RNAi transplastomic lines confirmed that homoplasmy has been achieved (FIG. 1d, 1e). However, in pLD-ATPase: RNA lines, A2 and A4 showed 4.0 kb fragment similar to wild type suggesting these two lines are negative lines while other three lines A5, B3 and B5 showed two bands, suggesting heteroplasmy (FIG. 10. All other transplastomic lines generated a single 5.6 kb hybridizing fragment suggesting they are homoplasmic.

Higher Level Transcription Level of dsRNA via the Chloroplast Genome

Figure 2A:
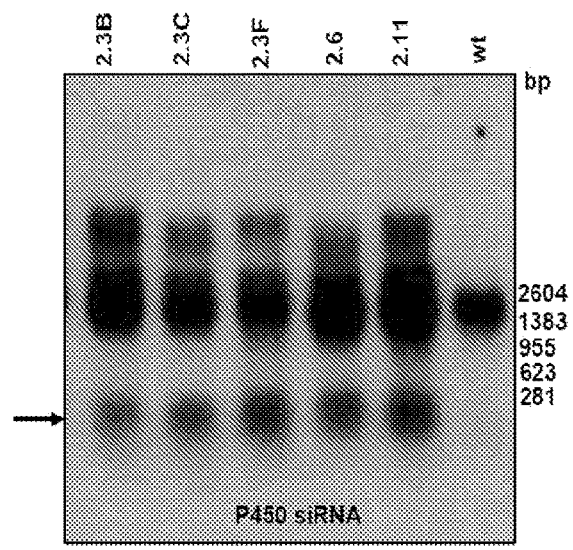
FIG. 2A-FIG. 2E.—Northern blot and Real-Time qRT-PCR analysis of ds RNA in transplastomic plants: For the northern blot, equal amount of 2 µg total RNA of every sample was loaded and separated on 1.0% denaturing agarose gel. The PCR amplified product from 3' psbA UTR was used as probe for northern blot.
Figure 2B:
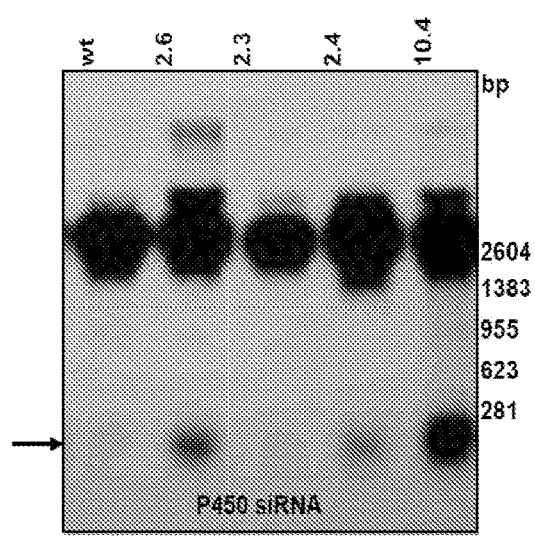
Figure 2C:
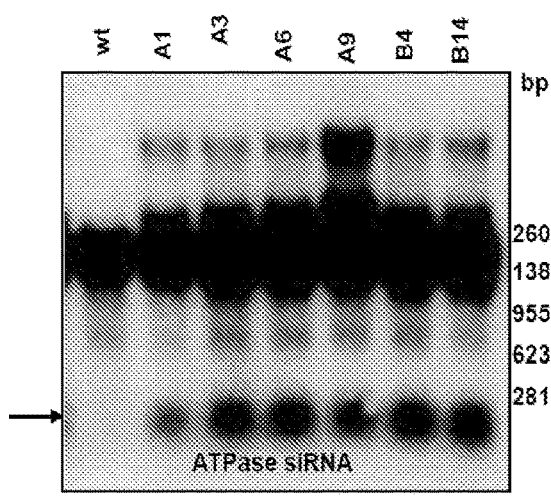

To investigate transcription and processing of the dsRNA via the tobacco chloroplast genome, northern hybridization analysis was done in the Southern blot-positive transplastomic lines, using 3' psbA UTR as the probe. Expected transcript sizes were detected in P450: RNAi (2.3, 2.4, 2.6, 2.11 and 10.4), ATPase: RNAi (A1, A3, A6, B2, B4, B5, B14) and Chi: RNAi (1 to 5) transplastomic lines while no dsRNA product was observed in WT (FIG. 2a-c). Both processed and unprocessed dsRNA transcripts were observed in all three dsRNA transplastomic lines. It is interesting to note that dsRNA transcripts (cleaved and unprocessed) were several fold higher than the highly expressed endogenous psbA gene. This may be due to double the copy number of transgenes (because of transgene insertion within the inverted repeat region) and transcription driven by the psbA promoter as well as the 16S rRNA promoter driving the entire ribosomal operon. Also, the cleaved dsRNA transcript was more abundant than the endogenous psbA transcript. The Northern blot positive transplastomic plants were used for insect feeding bioassays.

Figure 2D:
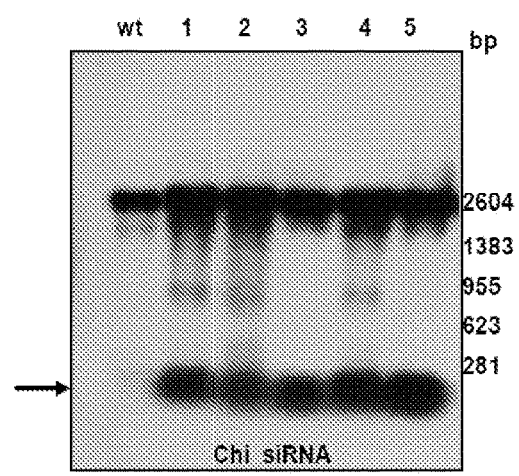
Figure 2E:
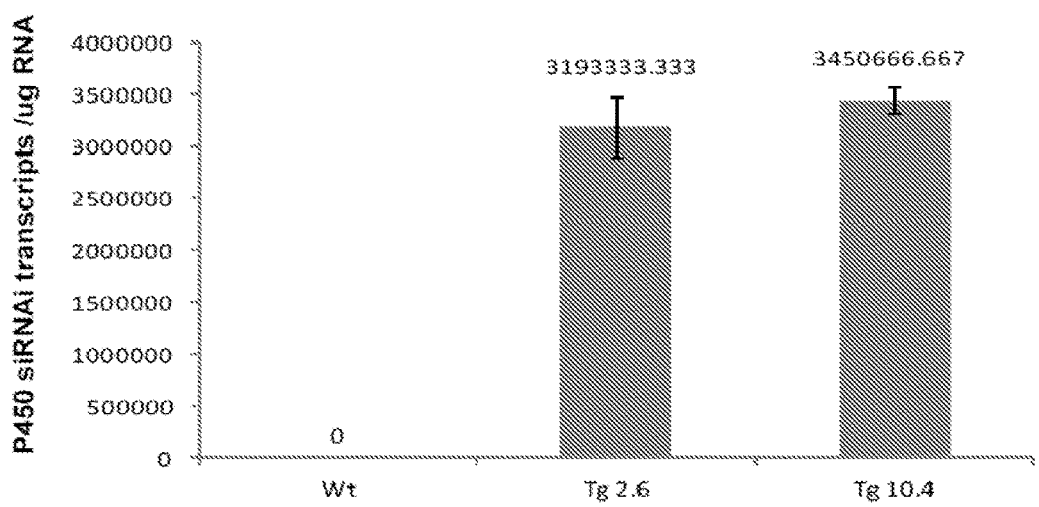
Figure 3A:
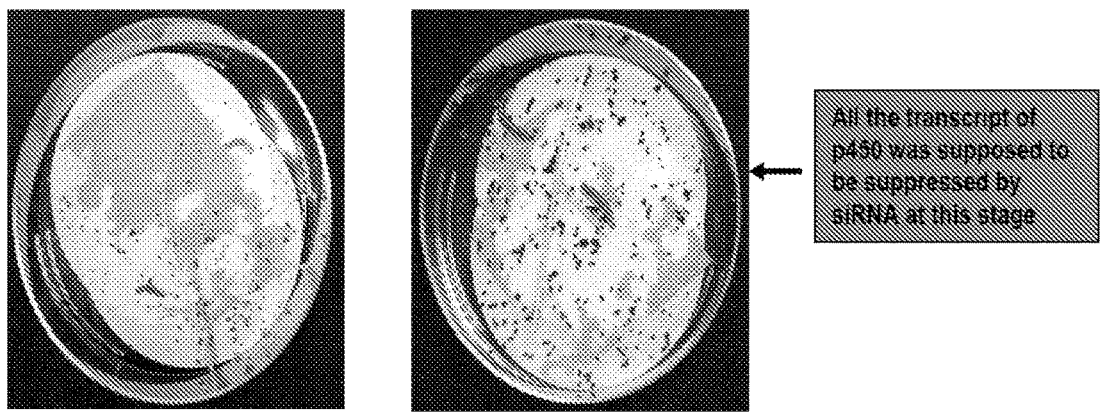
FIG. 3A-FIG. 3B. Strategy for P450: RNAi transplastomic plant insect bioassay. Two steps are needed for this insect bioassay. In the first step, third-instar larvae of Helicoverpa armigera were fed on P450: RNAi leaves for 4 days.
Figure 3B:
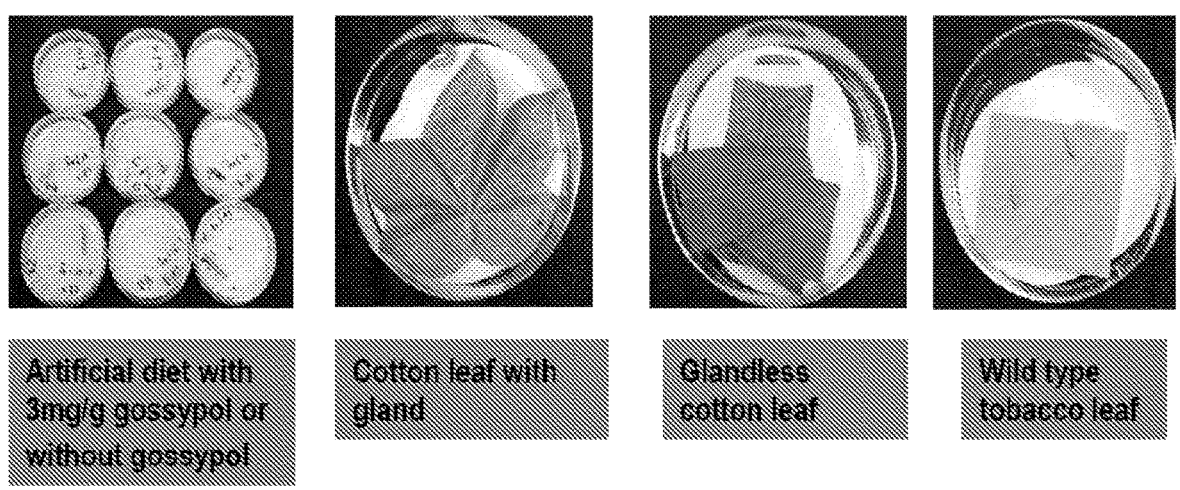
Figure 4A:
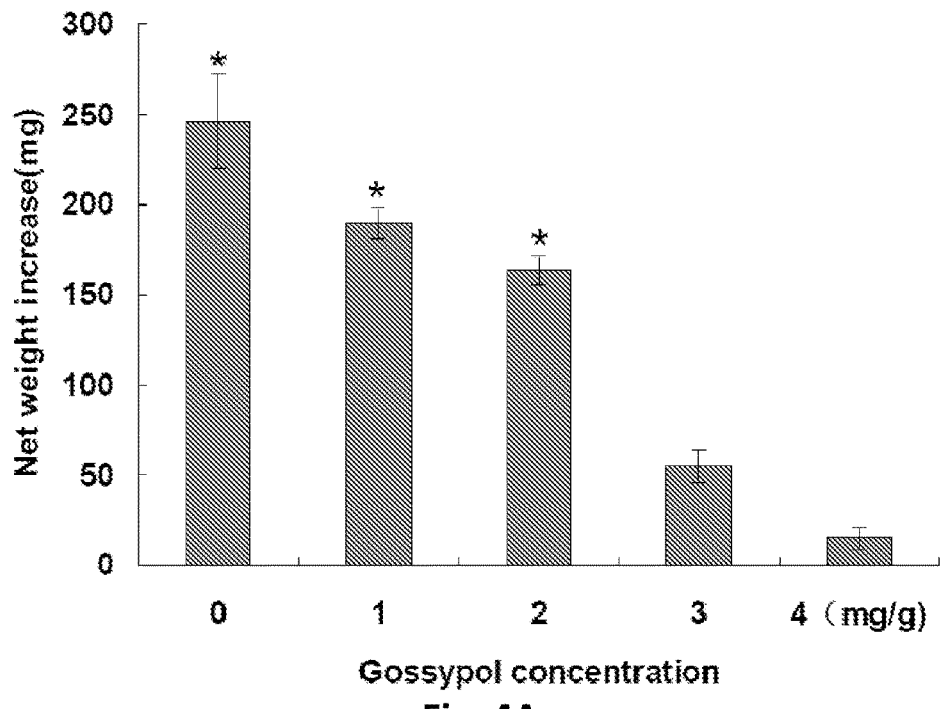
FIG. 4A-FIG. 4B. Effect of gossypol and siRNA on larval growth. The third-instar larvae were fed on P450: RNAi leaves for 4 days and were then transferred to the artificial diet or leaves (see the protocol in FIG. 3).
Figure 4B:
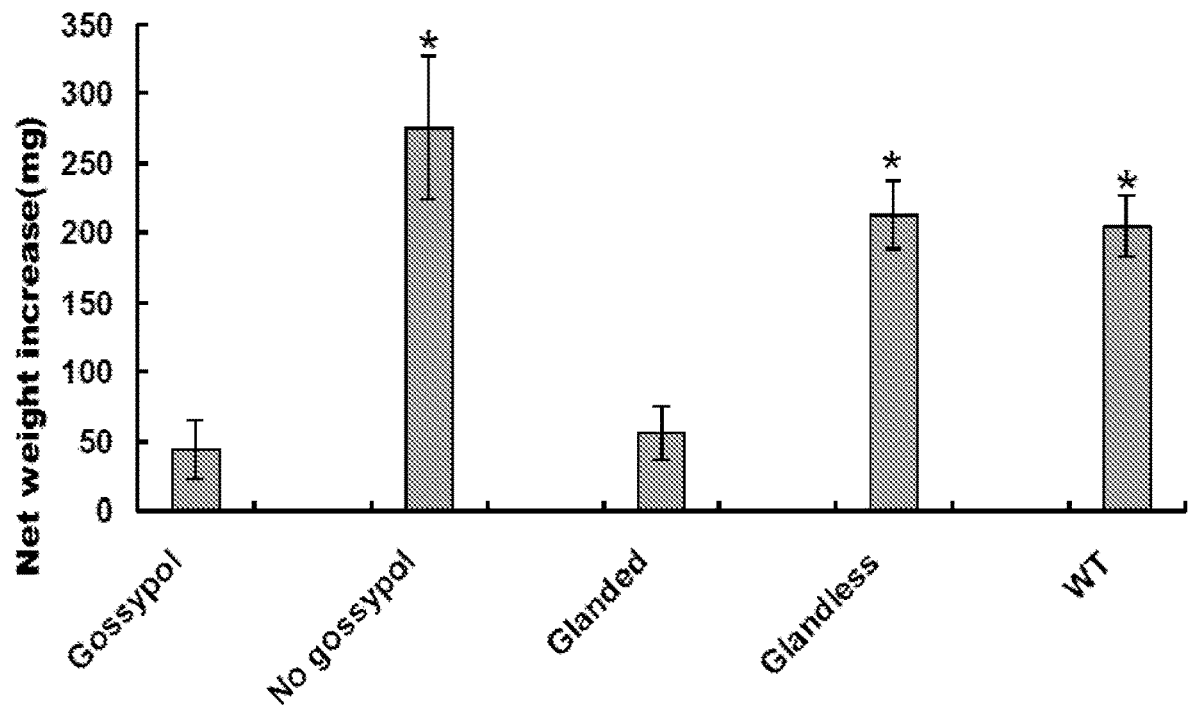
Figure 5A:
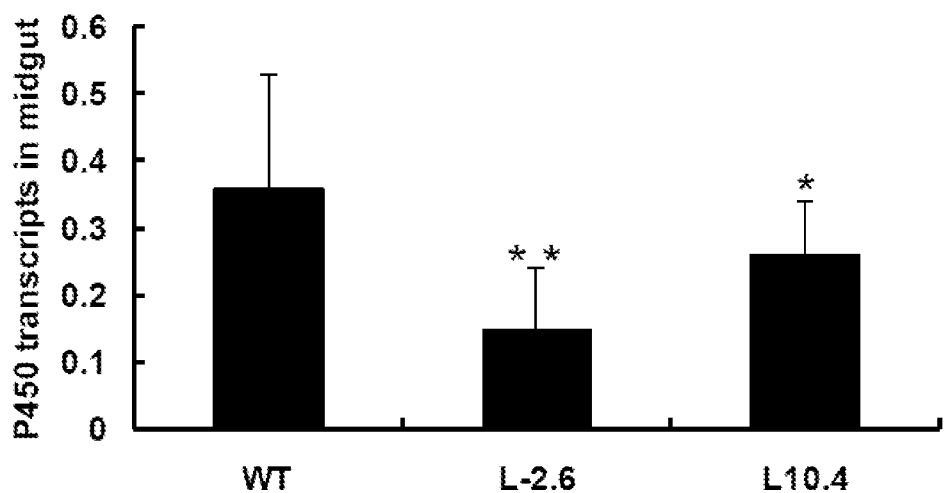
FIG. 5A-FIG. 5B. Quantity of P450 transcript in the midgut of tested larvae after feeding on the wild type and transplastomic leaves. The third-instars larvae were fed on transplastomic P450: RNAi or wild type tobacco leaves for 4 days or 7 days and then the midgut of these insects were isolated under stereomicroscope and then washed with ddH$_2$O to remove all the debris. The cleaned midgut tissues were stored in 70% ethanol at −20° C. RNA was isolated from these midgut tissues and used for Real-Time qRT-PCR analysis.
Figure 5B:
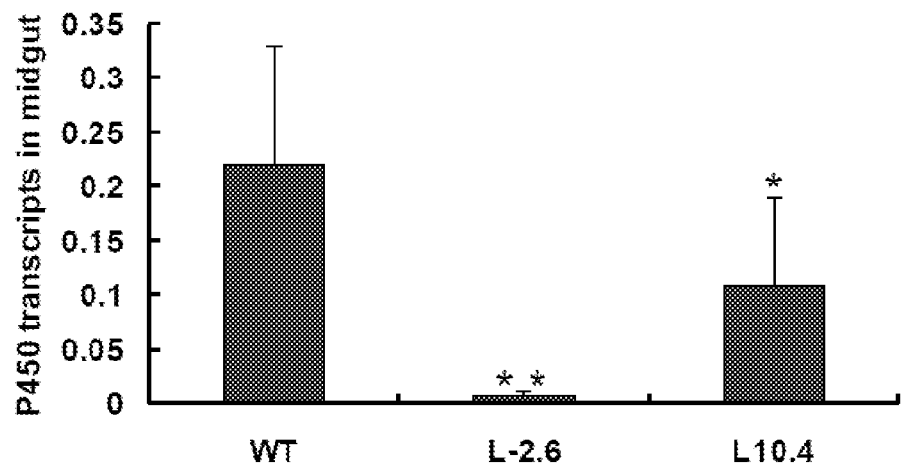
Figure 6A:
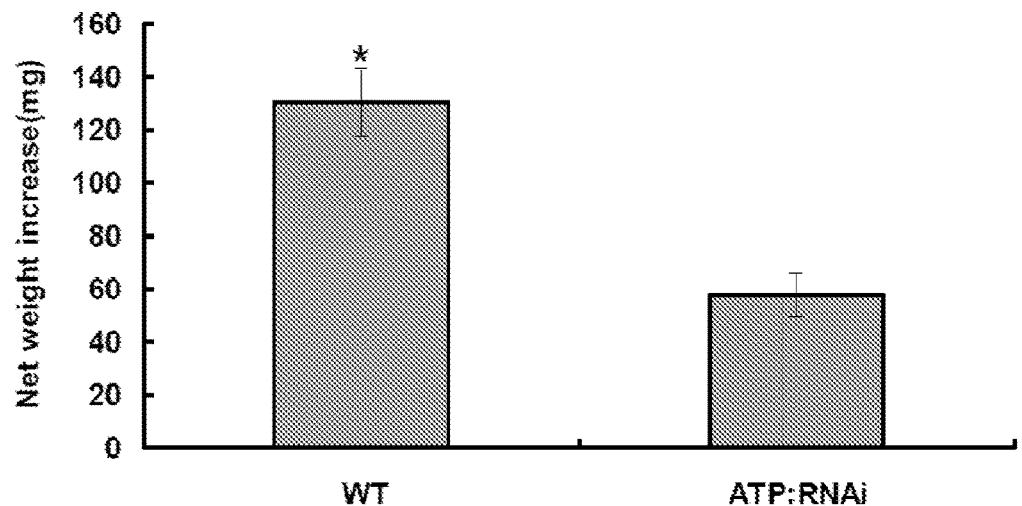
FIG. 6A-FIG. 6B. Net weight changes of Helicoverpa armigera feeding on transplastomic leaves expressing ATP and Chi dsRNAs.
Figure 6B:
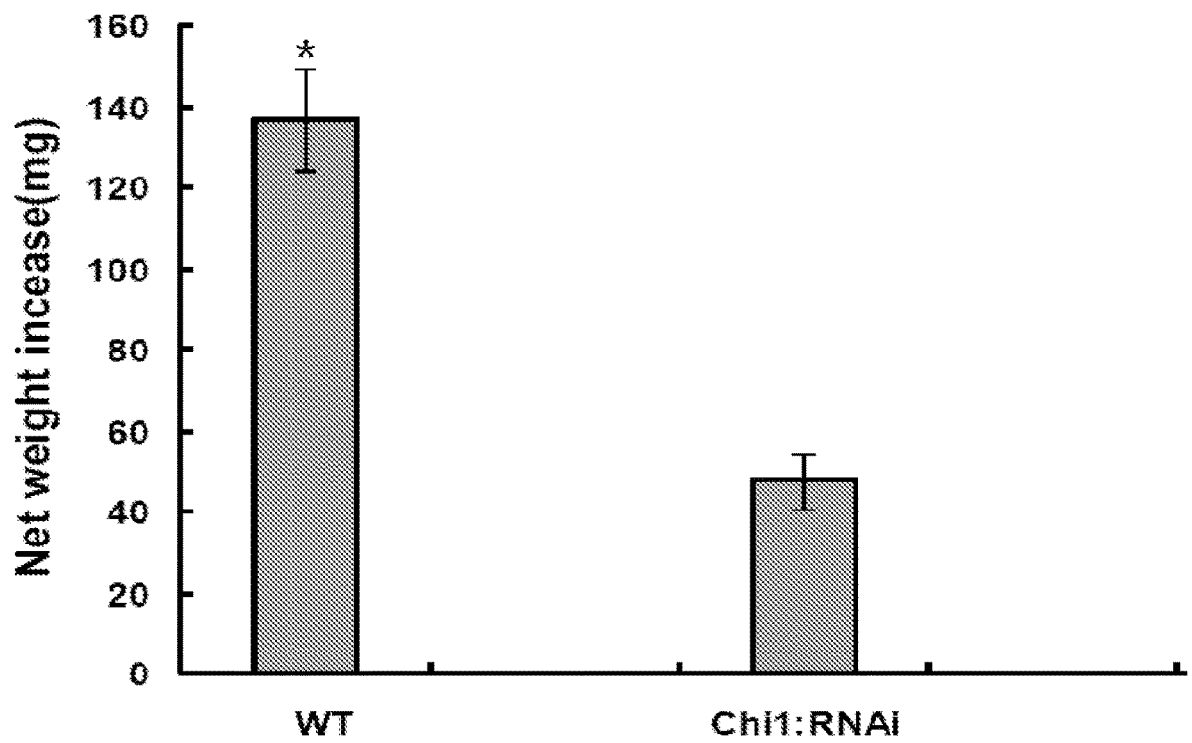
Figure 7A:
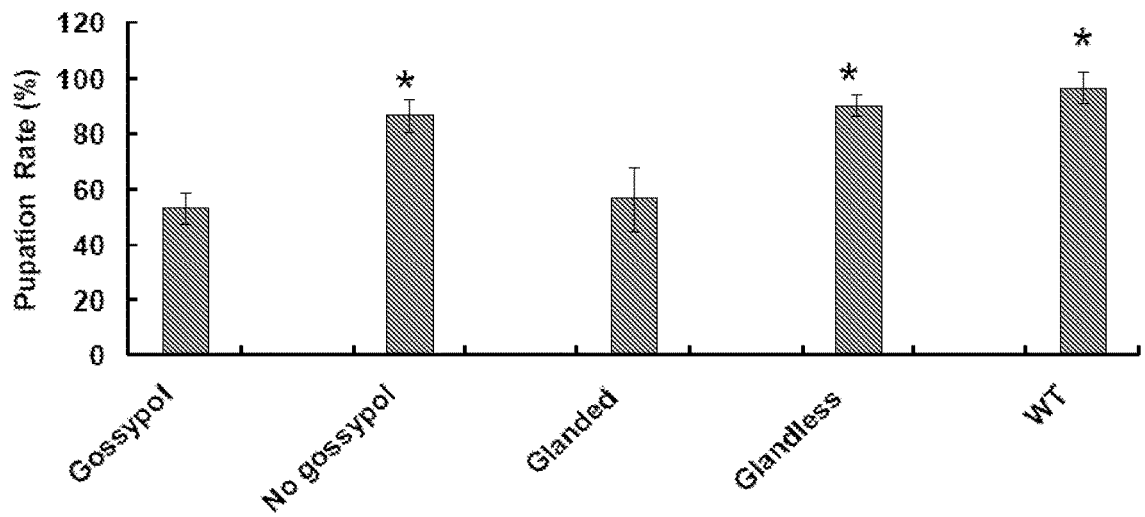
FIG. 7A-FIG. 7D. Larval development and insect mortality bioassay.
Figure 7B:
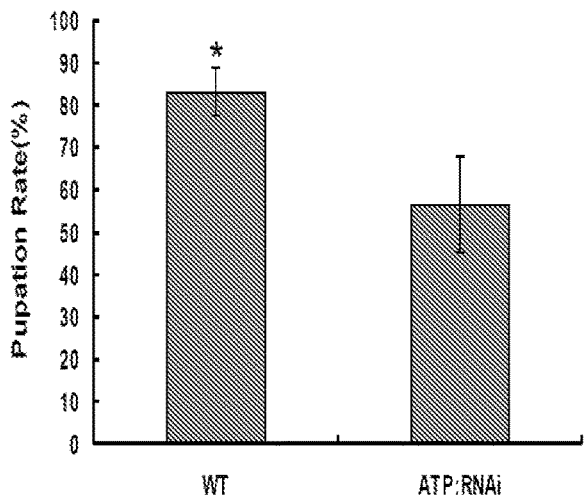
Figure 7C:
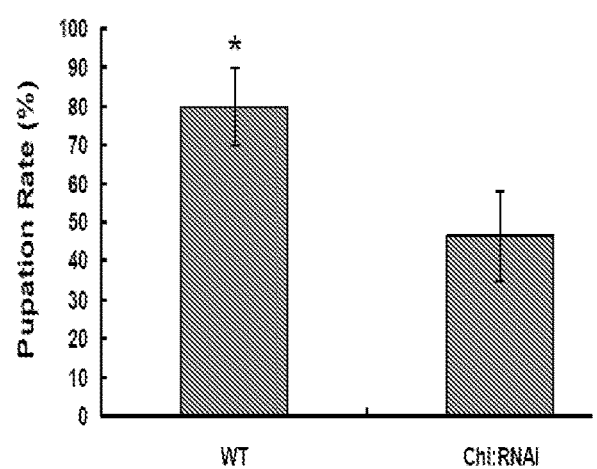
Figure 7D:
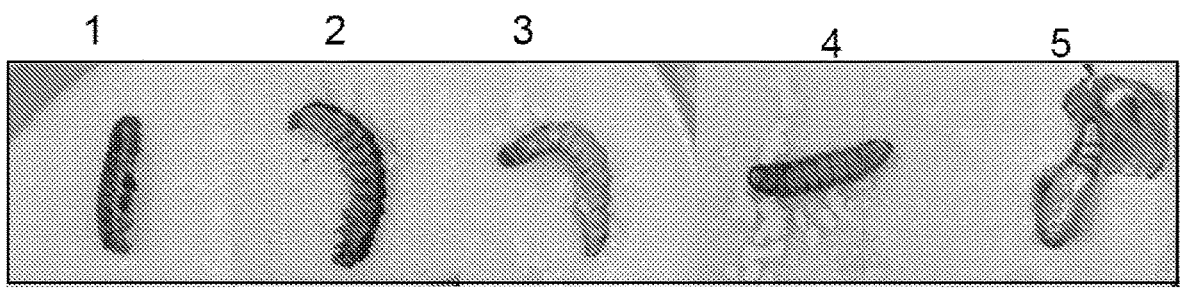

Real-Time PCR (qRT-PCR: Real-Time Quantitative Reverse Transcription PCR) analysis was performed to quantify the transcription level of dsRNAs. In this report, dsRNA of p450 gene was chosen for qRT-PCR analysis. These results showed that there was more than three million (3.19-3.45 millions) copies of P450 dsRNA in each microgram total RNA from transplastomic leaves, further confirming results observed in northern blots. However, cleaved dsRNA was not detected in the wild-type tobacco leaves (FIG. 2d), confirming probe specificity P450 Monooxygenase Suppression via Chloroplast dsRNA Feeding Reduced the *Helicoverpa Armigera* Tolerance to Gossypol Gossypol and related sesquiterpene biosynthesized in cotton are toxic to many organisms. However, most *Helicoverpa* insects resist gossypol because the P450 monooxygenases in the midgut of these insects permit them to tolerate the gossypol. Therefore, in order to suppress P450 gene, two step insect bioassay was conducted. In the first step, third-instar larvae of *Helicoverpa armigera* were fed on P450: RNAi expressed leaves for four days. Then, all these larvae were transferred to the following diet or leaves: artificial diet with 3 mg/g gossypol or without gossypol; cotton leaves with glands/glandless and wild-type tobacco leaves. Addition of gossypol in the artificial diet or in leaves affects the growth and development of the larvae (FIG. 3). For the gossypol tolerance test, the third-instar larvae of *Helicoverpa armigera* were fed on artificial diet supplemented with 0-4 mg/g of gossypol. These results showed that gossypol mediated toxicity to larvae were moderate. The weight increases (163-190 mg) on low concentration gossypol diet (1-2 mg/g) were comparable to respective controls (246 mg). However, the larval growth was dramatically suppressed at higher concentrations (3-4 mg/g) of gossypol diet with net weight increase of 15.1-55.4 mg (FIG. 4*a*). Thus, *Helicoverpa armigera* insects can tolerate relatively low concentration of gossypol. Therefore, 3 mg/g of gossypol concentration was used for subsequent insect bioassays.

Suppression of the P450 gene by dsRNA expressed via the chloroplast genome has been demonstrated herein. The transcription level of this targeted gene was assessed by qRT-PCR. After feeding on the two independent transplastomic lines (L2.6 and L10.4) for four days, the midgut of tested larvae were isolated and used for qRT-PCR analysis. The transcription level of the P450 gene located in the insect midgut was significantly decreased in both L2.6 ($P<0.01$) and L10.4-fed insects ($P<0.05$) (FIG. 5*a*). Similarly, the transcription level in both groups continued to decrease and the transcription of P450 in the L2.6 was too low to be detected in some samples (FIG. 5*b*).

In parallel experiments, other insects were subjected to the insect bioassay by feeding on different diet/leaves. The larval growth was significantly affected by the gossypol after four days of feeding on transplastomic leaves expressing dsRNA (FIG. 4*b*). The net weight increase of larvae fed on the diet supplemented with 3 mg/g of gossypol was 45 mg, which was one sixth of the net weigh increase when larvae fed on the diet without gossypol. Most *Gossypium* species store gossypol in the pigmented glands, but some glandless cultivars do not accumulate this toxin (Luo et al., 2001). Larvae fed with glanded leaves grew slower than those on the glandless leaves (net weight increase 56.5 mg vs 214 mg).

*Helicoverpa Armigera* Showed Stunted Development After Feeding on Leaves Expressing dsRNA-Chi and dsRNA-ATPase via the Chloroplast Genome For the Chi and ATPase: RNAi feeding bioassay, third-instar larvae were fed with the transplastomic leaves expressing dsRNA for 4 days. The bioassay results showed that siRNA significantly reduced *H. armigera* growth. The net weight increase of larvae fed on dsRNA-ATPase leaves was 57.7 mg within four days whereas it was 130.7 mg when fed on wild type untransformed leaves (FIG. 6*a*). Similarly, net weight increase of larvae fed with dsRNA-Chi expressing leaves was significantly ($P<0.05$) lower than those fed with wild type untransformed leaves. The average net increase of larvae fed on dsRNA-Chi leaves was 47.6 mg, whereas it was 136.7 when larvae were fed with wild type untransformed leaves (FIG. 6*b*). Silencing the P450, ATPase and Chi1 genes lead to the higher larvae mortality and lower pupation rate The transformation from larvae to pupae is a key step in the metamorphosis of *Helicoverpa* insects. In addition to the net weight increase of insects after feeding on different diet or leaves, the larval mortality and pupation rate were also observed in all treatment groups. After feeding with different diet or leaves for 4 days, all larvae were transferred to the artificial diet until pupation. During this transfer, some larvae failed to form pupae and finally died (FIG. 7*d,* 1-4 dead larvae). Only a few larvae developed into pupation stage (FIG. 7*d*, number 5 live pupa). The larvae (with P450 monooxygenase silencing) fed on the gossypol diet or glanded leaves showed significantly lower pupation rate ($P<0.05$) when compared to larvae fed on non-gossypol or glandless or wild type untransformed leaves (FIG. 7*a*).

The larval population decreased when the larvae were fed with transplastomic leaves expressing dsRNA-ATP and dsRNA-Chi for 4 days. During this growth period, some larvae moved slowly and stopped feeding and finally failed to complete the pupation. Only 56.7% of the larvae were successfully transformed into pupa after feeding with dsRNA-ATPase leaves whereas 83.3% of the larvae transformed to pupa when fed with wild type untransformed leaves (FIG. 7*b*). Similar bioassay results were obtained for insects fed with dsRNA-Chi expressing leaves. The pupation rate in the control group (80%) was significantly higher ($P<0.05$) than the dsRNA-Chi fed group (46.7%, FIG. 7*c*).

DISCUSSION

The expression of dsRNA via the chloroplast genome was successfully achieved for the first time as described herein. Most importantly, the qRT-PCR data provided direct proof of higher transcription level of dsRNA in the transplastomic cells, up to 3 5 million copies of dsRNA in one microgram (106 pg) RNA. Cleaved dsRNA is more abundant than the highly expressed endogenous chloroplast psbA gene. Higher accumulation of dsRNAs in plant cells is a requirement for the effective silencing of targeted genes.

The data presented here demonstrate that RNAi is a powerful tool for gene silencing and mediated post-transcriptional down-regulation of chitin synthases, P450 monooxygenase and V-ATPase gene transcripts and impact on development of larvae fed with transplastomic leaves. In the P450 bioassays, we observed that the P450 targeted transcripts in the insect midgut decreased significantly over time. The P450 transcript level of transplastomic lines 7-day-after feeding declined up to 92% when compared to respective controls. The correlation between dosage and effectiveness of RNAi have been shown in several siRNA injection studies (Boisson et al., 2006; Whyard et al., 2009; El-Shesheny et al., 2013). When compared to the in vitro spray/micro-injection of siRNA solution or feeding the artificial diet supplemented with siRNA, the transplastomic plant mediated RNAi offers several advantages: 1) higher doses of chloroplast-derived transcripts 2) stable expression throughout plant life cycle and 3) higher RNAi activity free from degradation of siRNA in vitro or in the digestive system due to bioencapsulation within plant cells.

Most importantly, we describe high abundance of dsRNA transcripts in transplastomic lines and their processing. Several lines of evidence support processing of dsRNA within chloroplasts, although unprocessed RNA is more abundant than cleaved transcripts. When primers specific for dsRNA transcript (P450/TpsbA) was used in qRT-PCR, dsRNA transcript products were observed in transplastomic lines but not in untransformed wild-type plants. Processed, cleaved and stabilized dsRNA with the 3'psbA UTR should be 272 nucleotides. Correct size of this transcript was observed in all three dsRNA transplastomic lines but not in untransformed wild-type plants. Because no inter-cistronic processing element was engineered, in the absence of processing only dicistron or polycistron transcripts should have been observed without any dsRNA cleavage and processing. According to our current understanding of processing of transgene transcripts (Martinez de Alba et al., 2013), after generation of primary transcripts, RISC complex cleaves mRNA and cleaved products are stabilized by SGS3; RDR6 then generates dsRNA and DCL2/4 form siRNA duplexes. However, none of these proteins are known to be present in plastids and yet we observed cleaved, stabilized and protected dsRNA products. So, it is possible that dsRNA processing occurs via a different mechanism in chloroplasts. Formation of stem-loop structure by dsRNA could leave single stranded regions for ribonucleolytic cleavage (Hotto et al., 2010). In addition, plastid non-coding RNAs (pncRNA) biogenesis relies on the assembly of RNases that generate mRNAs and rRNAs and are protected by secondary structures as well as RNA binding proteins (Hotto et al., 2012). In this case, dsRNA is further protected by the psbA 3′UTR, stabilizing this partially processed dsRNA product. Clearly, this ideal delivery system in which dsRNA is protected by bioencapsulation within plant cells represents an advance in the art of RNAi technology.

Recent development in transcriptomics, specifically strand-specific RNA sequencing by next generation sequence technology, have allowed high-throughput, comprehensive detection of low-abundance transcripts typical of the non-coding RNAs studied in eukaryotes and bacteria. Most recently, a few plastid pncRNAs had been identified (Zhao et al., 2007; Germain et al., 2011; Zhelyazkova et al., 2012) and even fewer had been investigated for functional role in gene regulation (Hegeman et al., 2005; Hotto et al., 2010; Zghidi-Abouzid et al., 2011). Another important source of pncRNA identification includes profiling 21-24 nt miRNAs and siRNAs (Shah et al., 2010; Hotto et al., 2012). Using RNA-Seq technology, pncRNAs of <40 nt were identified from *Arabidopsis* leaves, tomato fruit and flower barley leaf plastids and rice (*Oryza sativa*) leaves, respectively (Mohorianu et al., 2011; Ruwe and Schmitz-Linneweber, 2012; Zhelyazkova et al., 2012). Although there has been more pncRNA identification and pncRNA biogenesis, their functionality is still not clear. Till now, there is no evidence for an RNA interference pathway in plastids. However, bacteria could generate a size class of 20-50 nt ncRNAs termed (Clustered Regularly Interspaced Short Palindromic Repeats (CRISPRs), which are involved in silencing foreign genes.

Plant mediated RNAi has been an important crop protection strategy targeting insect pests with greater specificity than currently available pesticides or Bt toxin. Especially in the case of lepidopteran insect control, this technology has exhibited great potential. CYPs (e.g P450) was first successfully used to targeted genes to control lepidopteran insects, which could detoxify synthetic insecticide compounds such as gossypol in *Gossypium* plants. Several past reports showed that silencing these CYPs would suppress transcript levels of the targeted genes, attenuate their function, and finally decrease larval growth or survival (Mao et al., 2007, 2011; Zha et al., 2011; Kumar et al., 2012). Since CYPs belong to a multigene family, they have been proposed to be ideal targets for RNAi strategy (Kumar et al., 2012). Therefore, in this first attempt of gene silencing via the chloroplast genome, three dsRNA targets were selected as suitable candidate genes. In the present invention, successful silencing of three midgut lepidopteran insect genes with chloroplasts-derived dsRNA indicates that the plant-mediated RNAi approach is feasible via the chloroplast genome.

As described above, there is a great need to down-regulate harmful genes to confer protection against various plant pathogens. In addition, down regulation of out of control genes causing cancer or autoimmune diseases or immune disorders is highly desired in human health. Due to the high level of chloroplast transcription, a large amount of the dsRNA could be synthesized and orally delivered via bioencapsulation in plant cells to target disruption of harmful genes. To the best of our knowledge, there is no report on the expression the dsRNAs via the chloroplast genome. Taken together, results reported here demonstrate that the approach of chloroplast derived dsRNA will be useful not only in plant biotechnology but also in various biomedical applications.

REFERENCES FOR EXAMPLE I

Agrawal, P., Verma, D. and Daniell H. (2011) Expression of *Trichoderma reesei* β-mannanase in tobacco chloroplasts and its utilization in lignocellulosic woody biomass hydrolysis. PLoS One.6, e29302.

Aravin, A. A., Naumova, N. M., Tulin, A. V., Vagin, V. V., Rozovsky, Y. M. and Gvozdev, V. A. (2001) Double-stranded RNA-mediated silencing of genomic tandem repeats and transposable elements in the *D. melanogaster* germline. Curr. Biol. 11, 1017-1027.

Arlen, P. A., Singleton, M., Adamovicz, J. J., Ding, Y., Davoodi-Semiromi, A. and Daniell H. (2008) Effective plague vaccination via oral delivery of plant cells expressing F1-V antigens in chloroplasts. Infect Immun. 76, 3640-3650.

Bagasra, O. and Prilliman, K. R. (2004) RNA interference: the molecular immune system. J. Mol. Histol. 35, 545-53

Bale, J. S., Lenteren, J. C. and Bigler, F. (2008) Biological control and sustainable food production. Philos Trans R Soc Lond B Biol Sci. 363, 761-776.

Baum, J. A., Bogaert, T., Clinton, W., Heck, G. R., Feldmann, P., Ilagan, O., Johnson, S., Plaetinck, G., Munyikwa, T., Pleau, M., Vaughn, T. and Roberts, J. (2007) Control of coleopteran insect pests through RNA interference. Nat. Biotechnol. 25, 1322-1326.

Bernstein, E., Caudy, A., Hammond, S. and Hannon, G. (2001) Role for a bidentate ribonuclease in the initiation step of RNA interference. Nature, 409, 363-366.

Bettencourt, R., Terenius, O. and Faye, I. (2002) Hemolin gene silencing by ds-RNA injected into *Cecropia pupae* is lethal to next generation embryos. Insect Mol. Biol. 11, 267-271.

Boisson, B., Jacques, J. C., Choumet, V., Martin, E., Xu, J., Vernick, K. and Bourgouin, C. (2006) Gene silencing in mosquito salivary glands by RNAi. FEBS Lett. 580, 1988-1992.

Boyhan, D. and Daniell, H. (2010) Low cost production of proinsulin in tobacco and lettuce chloroplasts for injectable or oral delivery of functional insulin and c-peptide. Plant Biotechnol J. 9, 585-598.

Bravo, A. and Soberon, M. (2008) How to cope with insect resistance to Bt toxins? Trends Biotechnol. 26, 573-579.

Chen, X., Tian, H., Zou, L., Tang, B., Hu, J. and Zhang, W. (2008) Disruption of *Spodoptera exigua* larval development by silencing chitin synthase gene A with RNA interference. Bulletin of Entomological Research, 98, 613-619.

Clarke, J. L. and Daniell, H. (2011) Plastid biotechnology for crop production: present status and future perspectives. Plant Mol Biol. 76, 211-220.

Daniell, H. (2007) Transgene containment by maternal inheritance: effective or elusive? Proc Natl Acad Sci USA 104, 6879-6880.

Daniell, H., Datta, R., Varma, S., Gray, S. and Lee, S. B. (1998) Containment of herbicide resistance through genetic engineering of the chloroplast genome. Nat. Biotechnol. 16, 345-348.

Daniell, H., Khan, M. and Allison, L. (2002) Milestones in chloroplast genetic engineering: an environmentally friendly era in biotechnology. Trends Plant Sci. 7, 84-91.

Daniell, H., Lee, S. B., Panchal, T. and Wiebe, P. O. (2001) Expression of the native cholera toxin B subunit gene and assembly as functional oligomers in transgenic tobacco chloroplasts. J. Mol. Biol. 311, 1001-1009.

Daniell, H., Singh, N. D., Mason, H. and Streatfield, S. J. (2009) Plant-made vaccines and biopharmaceuticals. Trends Plant Sci. 14, 669-679.

Daniell, H., Kumar, S. and Dufourmantel, N. (2005) Breakthrough in chloroplast genetic engineering of agronomically important crops. Trends Biotechnol. 23, 238-245

Davoodi-Semiromi, A., Schreiber, M., Nallapali, S., Verma, D., Singh, N. D., Banks, R. K., Chakrabarti, D. and Daniell, H. (2010) Chloroplast-derived vaccine antigens confer dual immunity against cholera and malaria by oral or injectable delivery. Plant Biotech. J. 8, 223-242.

De Cosa, B., Moar, W., Lee, S. B., Miller, M. and Daniell, H. (2001) Overexpression of the Bt cry2Aa2 operon in chloroplasts leads to formation of insecticidal crystals. Nat. Biotechnol. 19, 71-74.

Dufourmantel, N., Dubald, M., Matringe, M., Canard, H., Garcon, F., Job, C., Kay, E., Wisniewski, J. P., Ferullo, J. M. and Pelissier, B. (2007) Generation and characterization of soybean and marker-free tobacco plastid transformants over-expressing a bacterial 4-hydroxyphenylpyruvate dioxygenase which provides strong herbicide tolerance. Plant Biotechnol J. 5, 118-133.

El-Shesheny, I., Hajeri, S., El-Hawary, I, Gowda, S. and Killiny, N. (2013) Silencing abnormal wing disc gene of the asian citrus psyllid, diaphorina citri disrupts adult wing development and increases nymph mortality. PLoS One, 8, e65392.

Fire, A., Xu, S. Q., Montgomery, M. K., Kostas, S. A., Driver, S. E. and Mello, C. C. (1998) Potent and specific genetic interference by double-stranded RNA in Caenorhabditis elegans. Nature, 391, 806-811.

Gahan, L. J., Gould, F. and Heckel, D. G. (2001) Identification of a gene associated with Bt resistance in Heliothis virescens. Science, 293, 857-860.

Germain, A., Herlich, S., Larom, S., Kim, S. H., Schuster, G. and Stern, D. B. (2011) Mutational analysis of Arabidopsis chloroplast polynucleotide phosphorylase reveals roles for both RNase PH core domains in polyadenylation, RNA 3-end maturation and intron degradation. Plant J. 67, 381-394.

Hegeman, C. E., Halter, C. P., Owens, T. G. and Hanson, M. R. (2005) Expression of complementary RNA from chloroplast transgenes affects editing efficiency of transgene and endogenous chloroplast transcripts. Nucleic Acids Res. 33, 1454-1464.

Hodgson, E., Rose, R. L., Ryu, D. Y., Falls, G., Blake, B. L. and Levi, P. E. (1995) Pesticide-metabolizing enzymes. Toxicol. Lett. 82/83, 73-81.

Hotto, A. M., Germain, A. and Stern, D. B. (2012) Plastid non-coding RNAs: emerging candidates for gene regulation. Trends in Plant Science, 17, 737-744.

Hotto, A. M., Huston, Z. E. and Stern, D. B. (2010) Overexpression of a natural chloroplast-encoded antisense RNA in tobacco destabilizes 5S rRNA and retards plant growth. BMC Plant Biol. 10, 213.

Jin, S. X. and Daniell, H. (2014) Expression of γ-tocopherol methyltransferase in chloroplasts results in massive proliferation of the inner envelope membrane and decreases susceptibility to salt and metal-induced oxidative stress by reducing reactive oxygen species. Plant Biotech. J. 12:1274-1285.

Jin, S. X., Zhang, X. L. and Daniell, H. (2012) Pinellia ternata agglutinin expression in chloroplasts confers broad spectrum resistance against aphid, whitefly, lepidopteran insects, bacterial and viral pathogens. Plant Biotech. J. 10, 313-327.

Jin, S. X., Kanagaraj, A., Verma, D., Lange, T. and Daniell, H. (2011) Release of hormones from conjugates: chloroplast expression of β-glucosidase results in elevated phytohormone levels associated with significant increase in biomass and protection from aphids or whiteflies conferred by sucrose esters. Plant Physiol. 155, 222-235.

Kohli, N., Westerveld, D. R., Ayache, A. C, Verma, A., Shil, P., Prasad, T., Zhu, P., Chan, S. L., Li, Q. H. and Daniell, H. (2014) Oral delivery of bioencapsulated proteins across blood-brain and blood-retinal barriers. Molecular therapy, 22, 535-546.

Kos, M., Loon, J. J., Dicke, M. and Vet, L. E. (2009) Transgenic plants as vital components of integrated pest management. Trends Biotechnol. 27, 621-627.

Kota, M., Daniell, H., Varma, S., Garczynski, S. F., Gould, F. and Moar, W. J. (1999) Overexpression of the Bacillus thuringiensis (Bt) Cry2Aa2 protein in chloroplasts confers resistance to plants against susceptible and Bt-resistant insects. Proc Natl Acad Sci USA 96, 1840-1845.

Kumar, P., Pandit, S. S. and Baldwin, I. T. (2012) Tobacco rattle virus vector: A rapid and transient means of silencing Manduca sexta genes by plant mediated RNA interference. PLoS One, 7, e31347.

Kwon, K. C., Nityanandam, R., New, J. S. and Daniell, H. (2013a) Oral delivery of bioencapsulated exendin 4 expressed in chloroplasts stimulates insulin secretion and lowers blood glucose level. Plant biotechnology Journal, 11, 77-86.

Kwon, K. C., Verma, D., Jin, S. X., Singh, N. D. and Daniell, H. (2013b) Release of proteins from intact chloroplasts induced by reactive oxygen species during biotic and abiotic stress. PLoS One, 8, e67106.

Kwon, K. C., Verma, D., Singh, N. D., Herzog., R. and Daniell, H. (2013c) Oral delivery of human biopharmaceuticals, autoantigens and vaccine antigens bioencapsulated in plant cells. Adv. Drug Deliv. Rev. 65, 782-799.

Lakshmi, P. S., Verma, D., Yang, X., Lloyd, B. and Daniell, H. (2013) Low cost tuberculosis vaccine antigens in capsules: expression in chloroplasts, bio-encapsulation, stability and functional evaluation in vitro. PLoS One, 8, e54708.

Lee, S. B., Li, B. C., Jin, S. X. and Daniell, H. (2011) Expression and characterization of antimicrobial peptides Retrocyclin-101 and Protegrin-1 in chloroplast to control viral and bacterial infections. Plant Biotechnol. J. 9, 100-115.

Lu, Y., Wu, K., Jiang, Y., Xia, B., Li, P., Feng, H., Wyckhuys, K. A. and Guo, Y. (2010) Mirid bug outbreaks in multiple crops correlated with wide-scale adoption of Bt cotton in China. Science, 328, 1151-1154.

Luo, P., Wang, Y. H., Wang, G. D., Essenberg, M. and Chen, X. Y. (2001) Molecular cloning and functional identification of (+)-delta-cadinene-8-hydroxylase, a cytochrome P450 mono-oxygenase (CYP706B1) of cotton sesquiterpene biosynthesis. Plant J. 28, 95-104.

Mao, Y. B., Tao, X. Y., Xue, X. Y., Wang, L. J. and Chen, X. Y. (2011) Cotton plants expressing CYP6AE14 double-stranded RNA show enhanced resistance to bollworms. Transgenic Research, 20, 665-673.

Mao, Y. B., Cai, W. J., Wang, J. W., Hong, G. J., Tao, X. Y., Wang, L. J., Huang, Y. P. and Chen, X. Y. (2007) Silencing a cotton bollworm P450 monooxygenase gene by plant-mediated RNAi impairs larval tolerance of gossypol. Nature Biotechnology, 25, 1307-1313.

Martinez de Alba, A. E., Elvira-Matelot, E. and Vaucheret, H. (2013) Gene silencing in plants: A diversity of pathways. Biochimica et Biophysica Acta, 1829, 1300-1308.

Merhige, P. M., Both-Kim, D., Robida, M. D. and Hollingsworth, M. J. (2005) RNA-protein complexes that form in the spinach chloroplast atpI 5' untranslated region can be divided into two subcomplexes, each comprised of unique cis-elements and trans-factors. Curr Genet. 48, 256-64.

Merzendorfer, H. (2006) Insect chitin synthases: a review. J. Comp. Physiol. B 176, 1-15.

Merzendorfer, H. and Zimoch, L. (2003) Chitin metabolism in insects: structure, function and regulation of chitin synthases and chitinases. J. Exp. Biol. 206, 4393-4412.

Mohorianu, I., Schwach, F., Jing, R., Lopez-Gomollon, S., Moxon, S., Szittya, G., Sorefan, K., Moulton, V., and Dalmay, T. (2011) Profiling of short RNAs during fleshy fruit development reveals stage-specific sRNAome expression patterns. Plant J. 67, 232-246.

Oey, M., Lohse, M., Kreikemeyer, B. and Bock, R. (2009) Exhaustion of the chloroplast protein synthesis capacity by massive expression of a highly stable protein antibiotic. Plant J. 57, 436-445.

Ohnishi, A., Hull, J. J and Matsumoto, S. (2006) Targeted disruption of genes in the Bombyx mori sex pheromone biosynthetic pathway. Proc Natl Acad Sci USA 103, 4398-4403.

Pitino, M., Coleman, A. D., Maffei, M. E., Ridout, C. J. and Hogenhout S. A. (2011) Silencing of aphid genes by dsRNA feeding from plants. PLoS One, 6, e25709.

Qaim, M. and Zilberman, D.(2003) Yield effects of genetically modified crops in developing countries. Science, 299, 900-902.

Ripoll, C., Favery, B., Lecomte, P., Van Damme, E., Peumans, W., Abad, P. and Jouanin, L. (2003) Evaluation of the ability of lectin from snowdrop (Galanthus nivalis) to protect plants against root-knot nematodes. Plant Sci. 164, 517-523.

Rothschild S I (2014) MicroRNA therapies in cancer. Molecular and Cellular Therapies 2: 7 Ruhlman, T., Ahangari, R., Devine, A., Samsam, M. and Daniell, H. (2007) Expression of cholera toxin B-proinsulin fusion protein in lettuce and tobacco chloroplasts-oral administration protects against development of insulitis in non-obese diabetic mice. Plant Biotechnol J. 5, 495-510.

Ruhlman, T., Verma, D., Samson, N. and Daniell, H. (2010) The role of heterologous chloroplast sequence elements in transgene integration and expression. Plant Physiol. 152, 2088-2104.

Ruiz, O. N., Alvarez, D., Tones, C., Roman, L. and Daniell, H. (2011) Metallothionein expression in chloroplasts enhances mercury accumulation and phytoremediation capability. Plant Biotechnol J. 9, 609-617.

Ruwe H. and Schmitz-Linneweber, C. (2012) Short non-coding RNA fragments accumulating in chloroplasts: footprints of RNA binding proteins. Nucleic Acids Res. 40, 3106-3116.

Saha, P., Majumder, P., Dutta, I., Ray, T., Roy, S. C. and Das, S. (2006) Transgenic rice expressing Allium sativum leaf lectin with enhanced resistance against sap-sucking insect pests. Planta, 223, 1329-1343.

Shah, A. A. Meese, E., Blin, N. (2010) Profiling of regulatory microRNA transcriptomes in various biological processes: a review. J. Appl. Genet. 51, 501-507

Shenoy, V., Kwon, K.-C., Rathinasabapathy, A., Lin, S., Jin, G., Song, C., Shil, P., Nair, A., Qi, Y., Li, Q., Francis, J., Katovich, M. J., Daniell, H. and Raizada, M. K. (2014). Oral delivery of angiotensin-converting enzyme 2 and angiotensin-(1-7) bioencapsulated in plant cells attenuates pulmonary hypertension. Hypertension, 64, 1248-1259.

Sherman, A., Su, J., Lin, S., Wang, X., Herzog, R. W. and Daniell, H. (2014) Suppression of inhibitor formation against factor VIII in hemophilia A mice by oral delivery of antigens bioencapsulated in plant cells. Blood 124: 1659-1668.

Shil, P. K., Kwon, K. C., Zhu, P., Verma, A., Daniell, H. and Li, Q. (2014) Oral delivery of ACE2/Ang-(1-7) bioencapsulated in plant cells protects against experimental uveitis and autoimmune uveoretinitis. Mol Ther. 22, 2069-2082.

Singh, N. D., Ding, Y. and Daniell, H. (2009) Chloroplast-derived vaccine antigens and biopharmaceuticals: Protocols for expression, purification, or oral delivery and functional evaluation. Methods Mol. Biol. 483, 163.

Tian, H., Peng, H., Yao, Q., Chen, H., Xie, Q., Tang, B. and Zhang, W. (2009) Developmental control of a lepidopteran pest Spodoptera exigua by ingestion of bacteria expressing dsRNA of a non-midgut gene. PLoS One, 4, 1-13.

Turner, C. T., Davy, M. W., MacDiarmid, R. M., Plummer, K. M., Birch, N. P. and Newcomb, R. D. (2006) RNA interference in the light brown apple moth, Epiphyas postvittana (Walker) induced by double-stranded RNA feeding. Insect Mol. Biol. 15, 383-391.

Verma, D. and Daniell, H. (2007) Chloroplast vector systems for biotechnology applications. Plant Physiol. 145, 1129-1143.

Verma, D., Jin, S. X., Kanagaraj, A., Singh, N. D., Daniel, J., Kolattukudy, P. E., Miller, M. and Daniell, H. (2013) Expression of fungal cutinase and swollenin in tobacco chloroplasts reveals novel enzyme functions and/or substrates. PLoS One, 8, e57187.

Verma, D., Kanagaraj, A., Jin, S., Singh, N. D., Kolattukudy, P. E. and Daniell H. (2010) Chloroplast-derived enzyme cocktails hydrolyse lignocellulosic biomass and release fermentable sugars. Plant Biotechnol J. 8, 332-350.

Verma, D., Samson, N. P., Koya, V. and Daniell, H. (2008) A protocol for expression of foreign genes in chloroplasts. Nat. Protoc. 3, 739-758.

Wang, Z. J., Dong, Y. C. Desneux, N. and Niu, C. Y. (2013) RNAi silencing of the HaHMG-CoA reductase gene inhibits oviposition in the Helicoverpa armigera cotton bollworm. PLoS One, 8, e67732.

Wesley, S. V., Helliwell, C. A., Smith, N. A., Wang, M. B., Rouse, D. T., Liu, Q., Gooding, P. S., Singh, S. P., Abbott, D., Stoutjesdijk, P. A., Robinson, S. P., Gleave, A. P., Green, A. G. and Waterhouse, P. M. (2001) Construct design for efficient, effective and high-throughput gene silencing in plants. Plant J. 27, 581-590.

Whyard, S., Singh, A. D. and Wong, S. (2009) Ingested double-stranded RNAs can act as species-specific insecticides. Insect Biochem. Mol. Biol. 39, 824-832.

Wu, K. M., Lu, Y. H., Feng, H. Q., Jiang, Y. Y. and Zhao, J. Z. (2008) Suppression of cotton bollworm in multiple crops in China in areas with Bt toxin-containing cotton. Science, 321, 1676-1678.

Wuriyanghan, H. and Falk, B. W. (2013) RNA interference towards the potato psyllid, Bactericera cockerelli, is induced in plants infected with recombinant tobacco mosaic virus (TMV). PLoS One, 8, e66050.

Xiong, Y., Zeng, H., Zhang, Y., Xu, D. and Qiu, D. (2013) Silencing the HaHR3 gene by transgenic plant-mediated RNAi to disrupt *Helicoverpa armigera* development. International Journal of Biological Sciences, 9, 370-381.

Zghidi-Abouzid, O., Merendino, L., Buhr, F., Malik-Ghulam, M. and Lerbs-Mache, S. (2011) Characterization of plastid psbT sense and antisense RNAs. Nucleic Acids Res. 39, 5379-5387.

Zha, W., Peng, X., Chen, R., Du, B., Zhu., L. and He, G. (2011) Knockdown of midgut genes by dsRNA-transgenic plant-mediated RNA interference in the hemipteran insect *Nilaparvata lugens*. PLoS One, 6, e20504.

Zhao, T., Li, G., Mi, S., Li, S., Hannon, G. J., Wang, X. J. and Qi, Y. (2007) A complex system of small RNAs in the unicellular green alga *Chlamydomonas reinhardtii*. Genes Dev, 21, 1190-1203.

Zhelyazkova, P., Hammani, K., Rojas, M., Voelker, R., Vargas-Suárez, M., Börner, T. and Barkan, A. (2012) Protein-mediated protection as the predominant mechanism for defining processed mRNA termini in land plant chloroplasts. Nucleic Acids Res. 40, 3092-3105.

Zhelyazkova, P., Sharma, C. M., Förstner, K. U., Liere, K., Vogel, J. and Börner, T. (2012) The primary transcriptome of barley chloroplasts: numerous noncoding RNAs and the dominating role of the plastid-encoded RNA polymerase. Plant Cell, 24, 123-136.

Zhu, J. Q., Liu S, Ma, Y., Zhang, J. Q., Qi, H. S., Wei, Z. J., Yao, Q., Zhang, W. Q. and Li S. (2012) Improvement of pest resistance in transgenic tobacco plants expressing dsRNA of an insect-associated gene EcR. PLoS One, 7, e38572.

Zimoch, L., Hogenkamp D. G., Kramer, K. J., Muthukrishnan, S. and Merzendorfer, H. (2005) Regulation of chitin synthesis in the larval midgut of *Manduca sexta*. Insect Biochem Mol Biol. 35, 515-527.

Zou, Z., Eibl, C. and Koop, H. U. (2003) The stem-loop region of the tobacco psbA 5'UTR is an important determinant of mRNA stability and translation efficiency. Mol Genet Genomics, 269, 340-349.

EXAMPLE II

Cloroplast Produced RNAi for Treatment of Human Disease

RNA interference (RNAi, siRNA, miRNA, shRNA, dsRNA) has great potential to be among the next generation of therapeutics for treating cancer and other genetic and viral diseases. The major obstacle blocking the clinical application of siRNA has been the development of an approach that is able to deliver sufficient siRNA to the cytoplasm of target cells in a form that is capable of eliciting a silencing effect. Prior attempts have focused on various delivery routes for RNAi including gene therapy, engineered nanoparticles, and conjugation with polymers. Thus far, none of these approaches has emerged as a safe and reliable solution for repeated delivery.

Until recently, the long standing paradigm in the digestion of nucleic acids has been that they are degraded into their basic building blocks and all genetic information is lost during digestion. Recently, results from several groups have challenged this model, demonstrating oral delivery of functional siRNA using nanoparticles and nanocarriers [29, 30]. Other studies have shown that miRNA contained in the exosomes of breast milk are stable in digestive conditions and are able to elicit an expansion of T cells when added to human blood. It has been demonstrated that double stranded RNA is resistant to acidity as low as pH 1 and is resistant to degradation by RNase [1, 26, 30]. Circulating miRNAs have also been shown to exist in a form extremely stable in serum and resistant to degradation by RNase, however naked miRNAs are rapidly degraded upon injection [33]. This suggests that circulating miRNAs may exist in complex with lipoproteins such as LDL or exist within microvesicles and exosomes.

*C. elegans* has long been known to respond to exogenous RNAi through dietary uptake. Feeding siRNA to *C. elegan* is able to achieve effective systemic silencing. Believed to act as an immune response to environmental pathogens, the uptake of RNAi in *C. elegans* is mediated by the transmembrane gate channel, SID-1 [10, 21]. In *C. elegans*, double-stranded RNA (dsRNA) passively enters cells through SID-1 to achieve systemic silencing of siRNA delivered through feeding [21, 25]. A lesser-studied SID-1 analogue, SIDT1 has been described in mammals to have extremely conserved homology and function as a miRNA transporter in mammals. It has been shown to mediate intercellular communication via miRNA within a tumor microenvironment [28]. Furthermore, overexpression of SIDT1 has been shown to mediate uptake of siRNA in human cancer cells [27, 32]. SIDT1 expression has not been characterized across different tissues in mammals, though several groups have suggested that it may have similar functions in mediating systemic RNAi effects.

RNAi provides a very potent and specific form of cancer therapy. RNAi can target any gene in a cell, including those that are currently undruggable by conventional therapeutics. The mechanism of mRNA degradation through the RNAi pathways allows a single RNAi molecule to destroy thousands of mRNA transcripts, making it an extremely efficient gene silencing mechanism. Currently, the major remaining hurdle for therapeutic use of RNAi is efficient in vivo intracellular delivery. In a recent study by Zhang et al., these investigators report that miRNA present in ingested rice was absorbed through the digestive tract, disseminated to a number of tissues around the body in microvesicles, and was able to suppress expression of LDLRAP1 (an LDL cholesterol uptake protein) through the silencing action of rice MIR168-a. Importantly, this silencing effect was abrogated upon introduction of an antisense MIR168-a strand, providing further evidence that the silencing of LDLRAP1 was indeed mediated by the exogenous MIR168-a. Other studies have also shown that a specific set of miRNAs are secreted into breast milk and are believed to influence the development of nursing infants.

Bioencapsulation of proteins in plant cells has previously been exploited in the oral delivery of therapeutic biologics [2], suggesting that this kind of protection can be utilized in oral delivery of RNAi. Furthermore, other groups have successfully delivered functional siRNA orally using siRNA encapsulated in engineered polymers and nanocarriers [29, 30], suggesting that targeted gene silencing can be achieved by oral delivery. These startling discoveries show that mammalian gene expression may be altered by the food that we eat, opening the possibility of exploiting these pathways to deliver therapeutic RNAi bioencapsulated in plant cells. MIR168-a has modest native expression levels in rice, and with a 13 base-pair overlap with the LDLRAP1 gene was able to elicit ~30% reduction in LDLRAP1 levels.

A novel route of oral delivery through the feeding of transgenic plants expressing high copy numbers of engineered RNAi is described herein. We have created RNAi constructs targeting GFP that can be fed to mice globally expressing GFP under a ubiquitin promoter. Uptake of various forms of RNAi across the GI tract, dissemination to tissues, and physiologic silencing response in mice are then assessed. The mechanism and specificity of uptake of various forms of RNAi (pre-miRNA, plant and animal miRNA, siRNA, shRNA) can be characterized to elucidate the mechanism and optimize design of improved therapeutic RNAi constructs. Silencing of GFP expression can demonstrate that this is a viable method of delivery for RNAi which can then be applied to a broad range of therapeutics. Delivery Kras RNAi using this delivery route will be assessed in mouse models of colon, lung, and pancreatic cancers. The exciting delivery route described herein for RNAi is cost effective, easily administered, and can solve many unmet medical needs.

Figure 8:
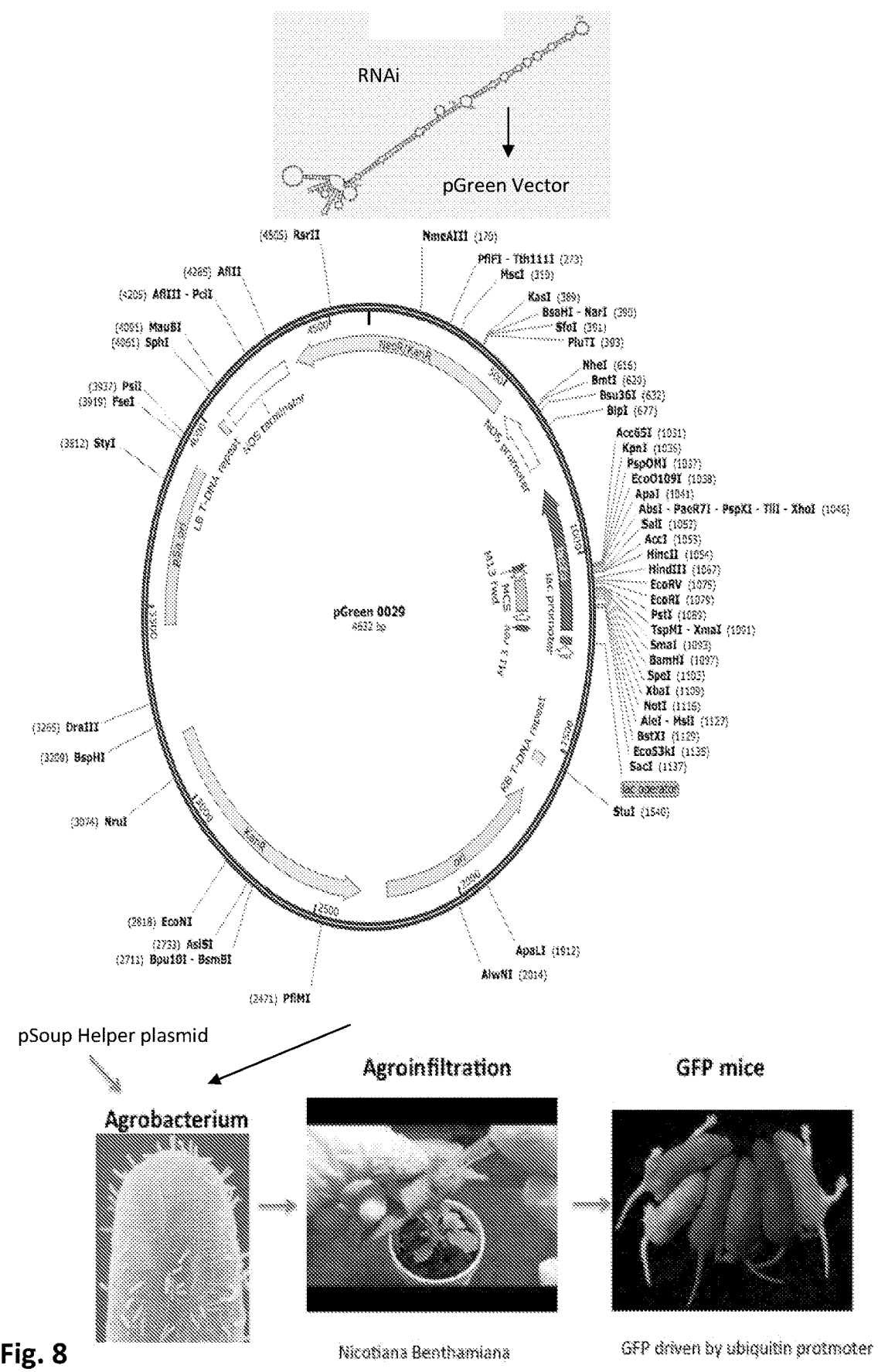
FIG. 8. Experimental design: shRNA oligos inserted into pGreen vector, co-transformed into Agrobacterium with pSoup helper vector, introduced into Nicotiana Benthaminana by Agroinfiltration, and fed to GFP mice by oral gavage.

RNAi Tissue Targeting, Silencing Effects and Therapeutic Potential in Cancer or Autoimmune Disorders Following Oral Delivery of Transgenic Plants Plant tissue from *Nicotiana benthamiana* expressing a GFP shRNA transgene is fed to globally-expressing GFP mice and dissemination and silencing assessed (FIG. 8).

Using a GFP marker and an RNAi construct with perfect complementarity to our target gene, we have a powerful system to study the uptake and dissemination of RNAi through oral delivery. Qualitative visual data through IHC as well as quantitative data from stem-loop QT-PCR, ELISA, and northern and western blots can be generated. The ability of exogenous siRNA from plants to enter circulation and silence expression of a reporter gene should further elucidate the silencing mechanism in mammals.

Figure 9:
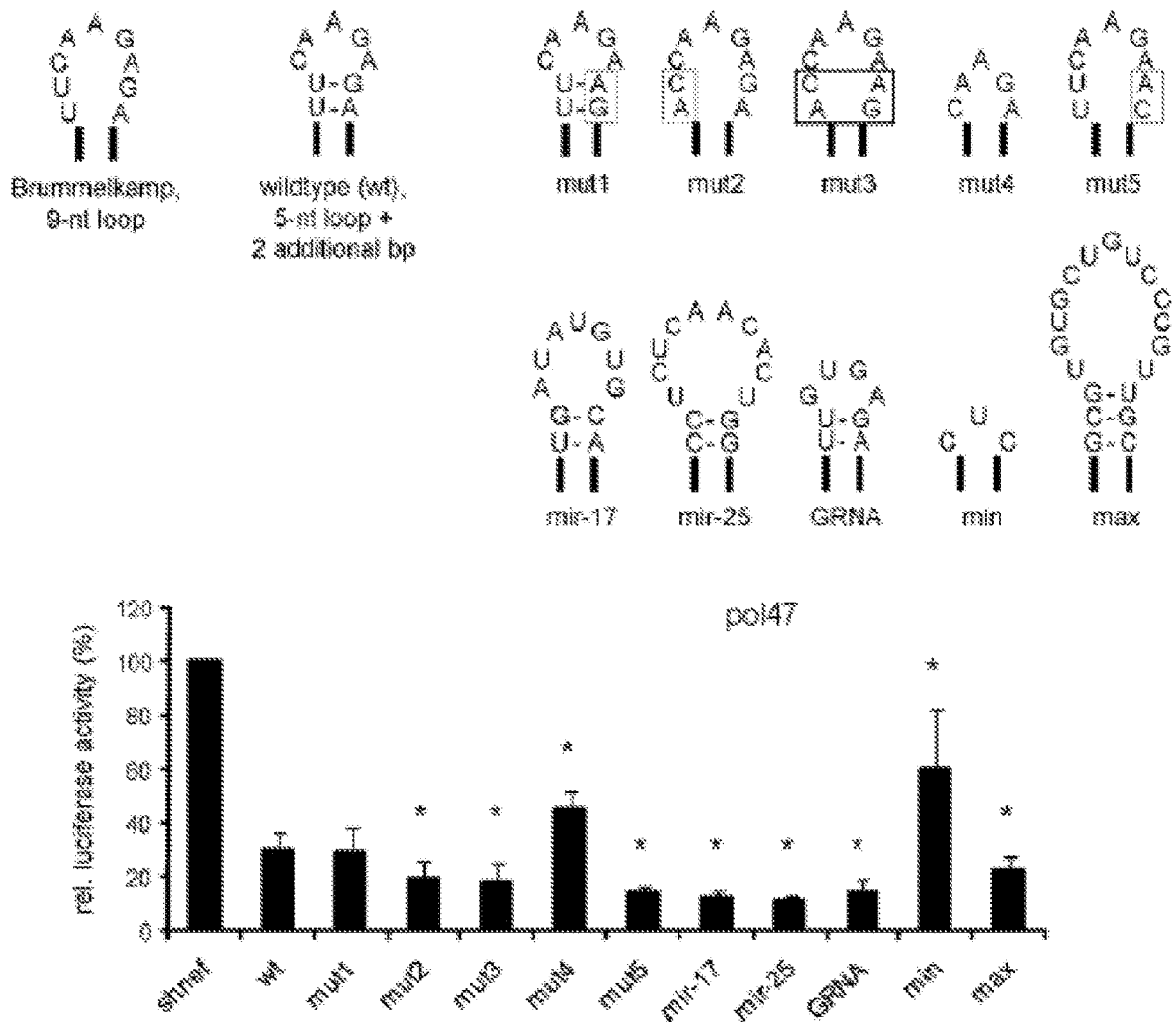
FIG. 9. Optimization of the shRNA stem-loop structure. The sequences of mir-17, mir-25 and max are reproduced as SEQ ID NOs: 18, 19 and 20, respectively. Additionally, the sequence of "UGAUAUGUGCA" provided at the bottom of FIG. 9 is reproduced as SEQ ID NO: 18.
Figure 11:
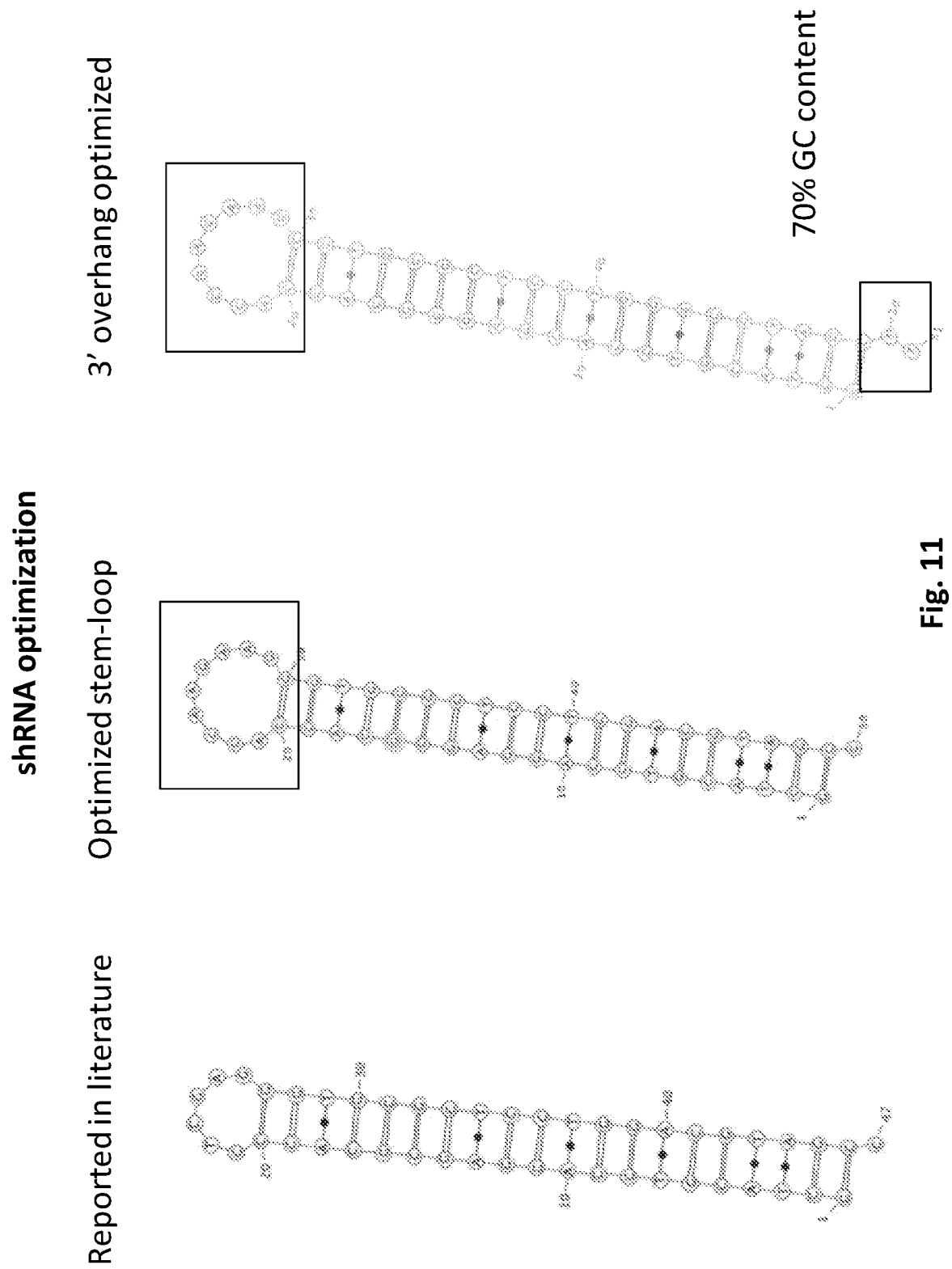
FIG. 11. shRNA constructs optimized to contain a 2nt TT 3' overhang. The sequences provided in FIG. 11, from left to right, are reproduced as SEQ ID NOs: 24 to 26, respectively.

We have designed shRNA constructs optimized on several parameters (stem-loop structure [47] (FIG. 9), high AT content (FIG. 10), and a 2 nt TT 3' overhang [48] (FIG. 11), while avoiding complementary sequences in the genome) targeting the coding region of our target genes. Parallel chloroplast vectors with target sequences are made as described in example 1. The 5' 'seed-sequence' of our shRNA (nt 2-8) should avoid complementarity to the 3' UTR of endogenous genes in the target host to avoid off-target silencing via miRNA pathways. The full length silencing sequence as well as the seed sequence is checked for homologous genes using a BLAST search and online algorithms to search for, and mimimize potential off target effects. To confirm that the observed silencing is indeed due to shRNA activity, mismatches can be introduced into the target sequence and to assess whether the silencing effect can be abrogated. Scrambled shRNA and empty vector will also be used as a negative control. We will initially evaluate our shRNA constructs in vitro by testing three silencing constructs in Caco2 cells transfected with a GFP plasmid under a ubiquitin promoter.

Figure 12:
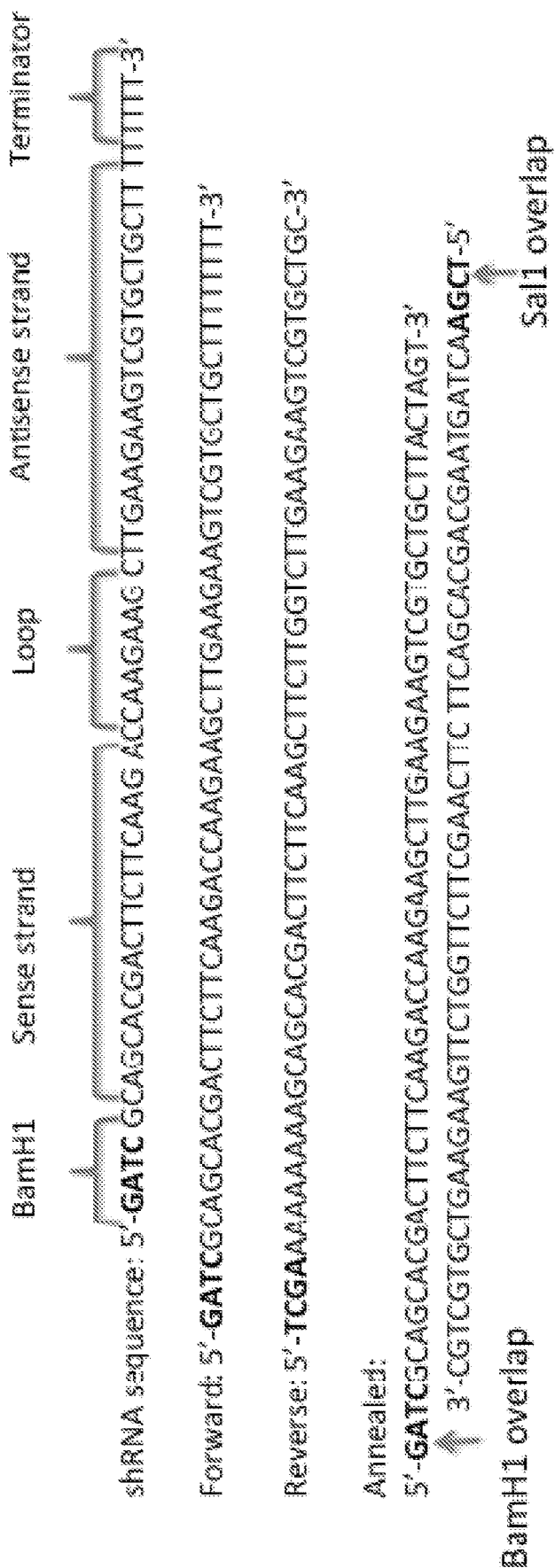
FIG. 12. Example of GFP shRNA constructed by oligo annealing for insertion into pGreen vector. The sequences listed in FIG. 12, from top to bottom, are reproduced as SEQ ID NOs: 27, 27, 28, 29, and 30, respectively.

In the case of GFP, shRNAs with the maximal silencing efficiency are selected which exhibit minimal off-target effects. To further evaluate off-target effects. To further evaluate our shRNA constructs, in vitro microarray analysis as previously described will be performed[50] (Agilent Human 1A V2 arrays). Using several constructs targeting different parts of the GFP gene, we will assess the targeting potential, effects on cell viability, and off target effects of each construct. Overlapping oligos were designed with 4 nt overhangs for the corresponding restriction sites (BamH1 and Sal1) to the pGreen vector (FIG. 12). To avoid the self-annealing of the individual oligo strands, oligos were annealed by heating the mixture to 95° C. for 10 minutes and allowing the mixture to cool overnight in a water bath to minimize self-annealing of the shRNA oligos.

Following ligation into the pGreen vector, the DNA is transformed into JM109 competent cells and cultured overnight in LB medium containing kanamycin. The *E. coli* is amplified and DNA is purified and transformed into LB4404 *Agrobacterium* competent cells by incubating with a pSoup helper plasmid for 5 minutes on ice, 5 minutes in liquid nitrogen, and 5 minutes at 37° C. *Agrobacterium* is grown at 28° C. for 48 hours in YEB medium containing kanamycin and streptomycin to select for transformed colonies. Transformed *Agrobacterium* is centrifuged and re-suspended in an MES infiltration medium, which is injected directly into the *N. benthamiana* using a syringe. Using this method, transgenic plants rapidly express high levels of the transcripts. In parallel, transplastomic lines expressing dsRNA are created by bombardment of chloroplast dsRNA vectors.

Figure 13:
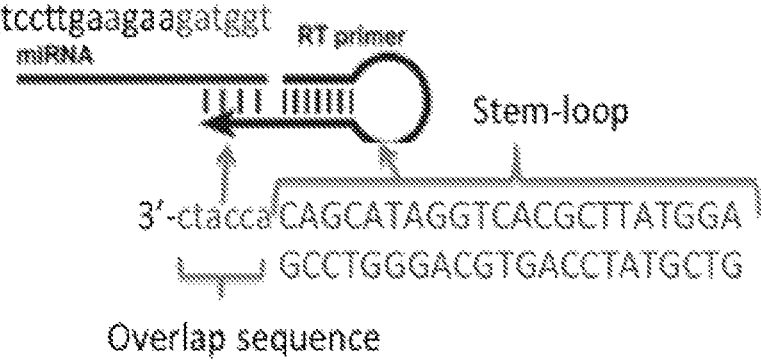
FIG. 13. Example of stem-loop primer design. 6nt segment overlaps with 3' end of mature miRNA. The sequences listed in FIG. 13, from top to bottom, are reproduced as SEQ ID NOs: 31, 32, 33 and 34, respectively.
Figure 15:
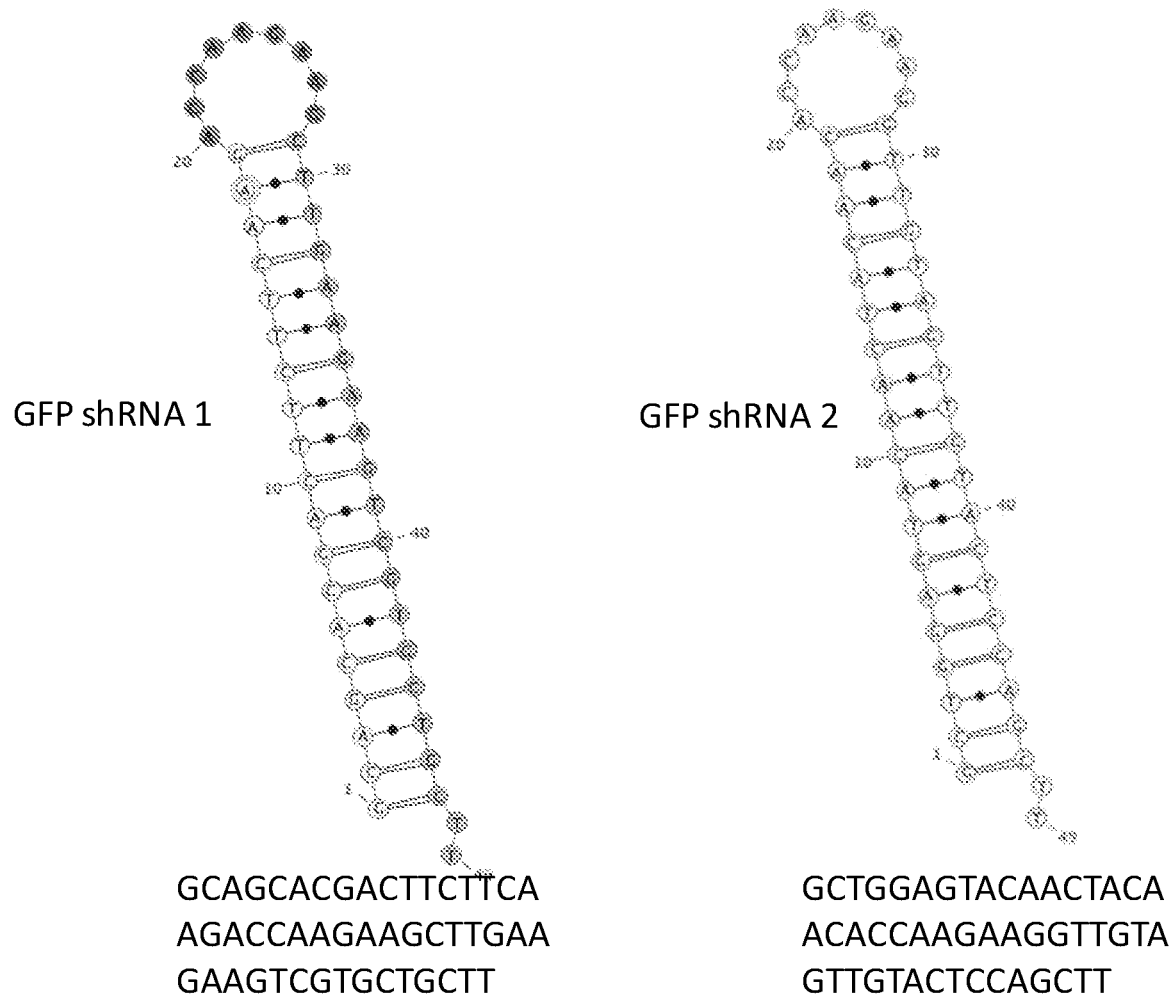
FIG. 15: GFP shRNA sequence confirmed by DNA sequence of the final vector. The sequence of GFP shRNA 1 is reproduced as SEQ ID NO: 36 while SEQ ID NO: 37 provides sequence of GFP shRNA 2.

RNA will be purified from leaves harvested from these GFP shRNA-expressing plants using Trizol and quantified by stem-loop QT-PCR for transcript expression levels and normalized to U6 snRNA and GAPDH to allow us to enable dosage setting. Stem-loop primers have been designed with a stem-loop structure containing a 6 nt overlap with the 3' end of the mature miRNA sequence, and a reverse primer overlapping the 12 nt on the 5' end (FIG. 13). To get an absolute concentration, a standard curve using known concentrations of synthetic oligos can be generated. The leaf material will be homogenized and suspended in PBS, then fed to genetically engineered mice that express GFP globally under a ubiquitin promoter. To evaluate the degree of GFP silencing and dose-dependency, groups of mice will be orally gavaged with a series of doses (based on dilutions of final concentration of transcript) of 200 μL of GFP-targeting transgenic plant material suspended in PBS. Serum will be collected in 2 hour intervals following feeding for 8 hours. Four days after receiving daily gavage, mice will be sacrificed and organs will be perfused and harvested. Protein and RNA will be extracted from tissue and analyzed by stem-loop qRT-PCR for GFP transcripts, as well as GFP ELISA and IHC to analyze protein levels. Silencing will be compared to GFP siRNA contained in liposomes delivered both orally and intravenously as a positive control and mice fed plants with *Agrobacterium* transformed with scrambled RNAi as a negative control.

Silencing of GFP over the course of a 4 day period of feeding GFP shRNA to mice is expected. Given that lyophilization increases the concentration of plant material ~10 fold, we estimate that the final concentration of RNAi should be ~75 fmol/g in order for this approach to be therapeutically relevant. This is ~13-fold higher than the expression of one of the more highly naturally expressed miRNAs, however this expression level is achievable given the high levels of expression using agroinfiltration [51] and the tightly controlled expression of endogenous miRNAs.

Since it was previously reported that significant silencing of a mammalian gene was achieved by a plant miRNA with imperfect complementarity and expressed at natural levels, we have designed an RNAi molecule with perfect complementarity and expect that overexpressing it will yield improved silencing effects. It has also been reported that siRNA with a 2'-O methylation have a reduction of ~80% in off-target effects [46], so we will include this modification in some of our designs for reducing off-target silencing effects of our RNAi. The 2'-O modification has also emerged as the preferred solution to immunogenicity and increase serum stability of circulating RNAi molecules, which will be a major benefit of using RNAi expressed in plant cells. Given that GFP has a 26 hour half-life, we expect that GFP levels will have dropped within this time period in cells that have received the GFP shRNA. Since this approach will only block the production of newly translated GFP, the transcript levels will be a more direct measure of the temporal efficacy of this experiment.

There is great need for an efficient method of silencing mutant Kras. Pancreatic cancer is among the deadliest types of tumors, the vast majority of which contain an activating mutation in the Kras gene. Although one of the most commonly mutated oncogenes in many forms of cancer, Kras is very difficult to target using conventional methods due to its nature as a GTPase. Based on this, Kras will be the first target tested therapeutically. Furthermore, a mutant-specific shRNA targeting Kras G12D will also be tested as this molecule should ameliorate side-effects associated with silencing wild-type Kras in healthy cells. Several other targets for cancer treatment include mTor, cMet, VEGF/VEGFR, c-kit, PDGF/PDGFR, P13K, HER2, EGFR and several other similar genes. siRNA encoding nucleic acids directed to these gene targets have been previously described. Vascular Endothelial Growth factor promotes angiogenesis and solid tumors. Several other specific targets include Ribonucleotide Reductase M2 (RRM2), kinesin spindle protein and VEGF, Polo-like kinase I (PLK1), tenascin-C, protein kinase N3, HIF-1 alpha, furin, etc. P53 is the most commonly activated tumor suppressor in different types of cancers. MDM2 is a negative antagonist of P53. Therefore, blocking MDM2 expression should be ideal for cancer treatment. Although synthetic siRNA are injected to achieve gene silencing in current research protocols, oral delivery of these dsRNA has not yet been investigated. Likewise, proinflamatory cytokines and other factors stimulate or cause several autoimmune disorders and allergies. There are several cytokines that could be down regulated using dsRNAs.

Kras is one among the most commonly mutated oncogenes. It maintains Kras GTPase in GTP-bound form and observed in >90% of pancreatic cancers as well as other tumors. Kras controls several downstream proliferation and growth pathways. MiR-34 is an ideal Kras target. The siRNA has high specificity to distinguish between Kras and mutant Kras containing a single point mutation.

We have generated Kras shRNA-vectors for transient viral expression or stable dsRNA expression via the chloroplast genome. The RNAi constructs can be tested in the PDAC cancer cell line. Recombinant plant material can also be fed to genetically engineereded KPC mice which provide a model of pancreatic cancer. adenoCre inducible Kras G12D mouse model of lung cancer, and a Kras/APC/p53 mouse model of colon cancer will also be tested. In addition, we have designed mutant-specific Kras shRNA to target the G12D mutation in genetic mouse models to determine whether we can specifically target a mutant oncogene while sparing the wild type gene.

The constructs will be delivered as described above. Mutant-specific Kras have been previously described [54], taking advantage of the loss of nuclease activity that occurs with a mismatch at the nucleotide corresponding to the cleavage site of the target transcript. Screening for off-target effects can optionally also be performed. We expect that the mouse model for lung and colon cancer will exhibit the greatest physiologic effects using this approach. Since Kras is associated with EMT and metastasis, we expect that tumors will exhibit less epithelial to mesenchymal transition (EMT) in treated mice (upregulation of E-cadherin and downregulation of EMT markers such as Zeb1) and decreased number of metastases. Plant-derived miRNA is modified with a 2'-O methyl group. This modification has been used in the delivery of siRNA to improve the siRNA stability in circulation as well as reducing its immunogenic effects, so we expect that this form of RNAi will have superior pharmacokinetic properties once in circulation as compared with synthetic siRNA, and will minimize immunologic response to the foreign RNAi [45].

Characterization of the Mechanism and Specificity of RNAi Uptake in the GI Tract SID-1 is a transmembrane channel protein known to mediate intestinal RNAi uptake in *C. elegans*, acting as the gateway to systemic RNAi silencing in the worms. A highly homologous protein, SIDT1, is known to exist in mammals including humans. SIDT1 appears to be the most likely candidate responsible for mediating uptake of miRNA in the GI tract, yet this protein remains largely unstudied. Overexpression of SIDT1 has been shown to enhance uptake of siRNA in mammalian cells, but its expression has not been characterized in mammals [27, 32]. SIDT1 expression in the subsections of the small and large intestine will be studied. Since it is believed that miRNA in breast milk is taken up by nursing infants, it is possible that this receptor is overexpressed in infancy. For this reason, we will also compare expression levels of nursing mice to adult mice.

Strategic design of RNAi molecules for delivery through the oral pathway will benefit from a greater understanding of processing of RNAi in plant cells and uptake of various forms of RNAi in the GI tract. In vitro experiments to test the uptake of various forms of RNAi molecules by transfecting Caco-2 intestinal epithelial cells with a SIDT1 using pCMV plasmid as previously described will be performed [28]. We will then expose the cells to homogenized plant tissue expressing various forms of RNAi: plant and animal miRNA in pri-miRNA, pre-miRNA, and mature forms, and shRNA of various lengths (FIG. 12 and FIG. 13). The final processed form of these constructs will be evaluated in plant cells by step-loop QT-PCR and Northern blot. 'Chimeric' miRNA that we have created which has the secondary structure backbone of plant miR156a with a modified targeting sequence based on our target will also be tested. Furthermore we will test the uptake of naked mature miRNA as compared to mature miRNA in complex with Ago2.

Since SIDT1 has been shown to act as a passive factor for RNAi, we expect that expression of SIDT1 in Caco2 cells would facilitate the uptake of RNAi and transport across the cell. Based on previous studies [1], we expect that the RNAi will be packaged in exosomes shed from the cells. Further, we expect that silencing SIDT1 would abrogate the RNAi uptake effect. Based on previous studies, we believe that mature miRNA will be taken up by the SIDT1 receptor and not pre-miRNA or other forms. We expect that the 'chimeric' miRNA created based on the most abundantly disseminated miRNAs in previous studies will yield the mature miRNA most likely to be taken up in the GI tract (FIG. 14).

REFERENCES

1. Lin Zhang et al. Exogenous plant MIR168a specifically targets mammalian LDLRAP1: evidence of cross-kingdom regulation by microRNA. Cell Research (2011):1-20
2. Kwang-Chul Kwon et al. Oral delivery of human biopharmaceuticals, autoantigens and vaccine antigens bioencapsulated in plant cells. Advanced Drug Delivery Reviews. Volume 65, Issue 6, 15 Jun. 2013, Pages 782-799

3. Mengxi Jiang, Xiaolin Sang, and Zhi Hong. Beyond nutrients: Food-derived microRNAs provide cross-kingdom regulation. Bioessays 34: 280-284
4. Bin Yu et al. Methylation as a Crucial Step in Plant microRNA Biogenesis. Science 307, 932 (2005);
5. Kenneth W. Witwer. XenomiRs and miRNA homeostasis in health and disease. RNA Biology 9:9, 1147-1154; September 2012
6. Jinsong Zhang & Li Ma. MicroRNA control of epithelial-mesenchymal transition and metastasis. Cancer Metastasis Rev. June 2012
7. Jennifer S. Whangbo and Craig P. Hunter. Environmental RNA interference. Trends in Genetics Vol. 24
8. Anna M. Hoy and Amy H. Buck. Extracellular small RNAs: what, where, why? Biochemical Society Transactions (2012) Volume 40, part 4
9. Martin J. O'Neill, Ludovic Bourre, Silvia Melgar and Caitriona M. O'Driscoll. Intestinal delivery of non-viral gene therapeutics: physiological barriers and preclinical models. Drug Discovery Today. Volume 16, Numbers 5/6. March 2011 REVIEWS
10. Mark S. Duxbury, Stanley W. Ashley, Edward E. Whang. RNA interference: A mammalian SID-1 homologue enhances siRNA uptake and gene silencing efficacy in human cells. Biochemical and Biophysical Research Communications 331 (2005) 459-463
11. Taketoshi Hata, Kosuke Murakami, Hajime Nakatani, Yasunari Yamamoto, Tsukasa Matsuda, Naohito Aoki. Isolation of bovine milk-derived microvesicles carrying mRNAs and microRNAs. Biochemical and Biophysical Research Communications 396 (2010) 528-533
12. Y-N Liu et al. MiR-1 and miR-200 inhibit EMT via Slug-dependent and tumorigenesis via Slug-independent mechanisms. Oncogene (2013) 296-306
13. Laura García-Segura, Martha Pérez-Andrade, Juan Miranda-Ríos. The Emerging Role of MicroRNAs in the Regulation of Gene Expression by Nutrients. J Nutrigenet Nutrigenomics 2013; 6:16-31
14. Muller Fabbri et al. MicroRNAs bind to Toll-like receptors to induce prometastatic inflammatory response. PNAS. July 2012
15. Mehmet Fatih Bolukbasi et al. miR-1289 and "Zipcode"-like Sequence Enrich mRNAs in Microvesicles. Molecular Therapy-Nucleic Acids (2012) 1, e10
16. Peter Järver et al. Peptide-mediated Cell and In Vivo Delivery of Antisense Oligonucleotides and siRNA. Molecular Therapy-Nucleic Acids (2011) 1, e27
17. Nicolas G. Bologna, Arnaldo L. Schapire and Javier F. Palatnik. Processing of plant microRNA precursors. BRIEFINGS IN FUNCTIONAL GENOMICS. VOL 12. NO 1. 37
18. Kendal D. Hirschi. New foods for thought. Trends in Plant Science March 2012, Vol. 17, No. 3
19. Shuanglin Xiang, Johannes Fruehauf & Chiang J Li. Short hairpin RNA-expressing bacteria elicit RNA interference in mammals. NATURE BIOTECHNOLOGY VOLUME 24 NUMBER 6 JUNE 200
20. Andrew D. Rhim. EMT and Dissemination Precede Pancreatic Tumor Formation. Cell 148, 349-361, Jan. 20, 2012
21. Joseph D. Shih and Craig P. Hunter. SID-1 is a dsRNA-selective dsRNA-gated channel. RNA 2011 17: 1057-1065
22. Lydia Alvarez-Erviti et al. Delivery of siRNA to the mouse brain by systemic injection of targeted exosomes. Nature biotechnology VOLUME 29 NUMBER 4 Apr. 2011
23. Thijn R. Brummelkamp, et al. A System for Stable Expression of Short Interfering RNAs in Mammalian Cells. Science 296, 550 (2002)
24. Brian D. Brown and Luigi Naldini. Exploiting and antagonizing microRNA regulation for therapeutic and experimental applications. NATURE REVIEWS Genetics V10 August 2009
25. William M. Winston, Christina Molodowitch, Craig P. Hunter. Systemic RNAi in C. elegans Requires the Putative Transmembrane Protein SID-1. Science 29 March 2002
26. Nobuyoshi Kosaka, Hirohisa Izumi, Kazunori Sekine, Takahiro Ochiya. microRNA as a new immune-regulatory agent in breast milk. Silence 2010 1:7
27. Duxbury M S1, Ashley S W, Whang E E. RNA interference: a mammalian SID-1 homologue enhances siRNA uptake and gene silencing efficacy in human cells. Biochem Biophys Res Commun. 2005 Jun. 3; 331(2): 459-63.
28. Mohamed O. Elhassan, Jennifer Christie and Mark S. Duxbury. Homo sapiens Systemic RNA Interference-defective-1 Transmembrane Family Member 1 (SIDT1) Protein Mediates Contact-dependent Small RNA Transfer and MicroRNA-21-driven Chemoresistance. Feb. 17, 2012 The Journal of Biological Chemistry, 287, 5267-5277.
29. Myriam Aouadi, Gregory J. Tesz, Sarah M. Nicoloro, Mengxi Wang, My Chouinard, Ernesto Soto, Gary R. Ostroff & Michael P. Czech. Orally delivered siRNA targeting macrophage Map4k4 suppresses systemic inflammation. Nature Vol. 458:30 April 2009
30. Borja Ballarín-González, Frederik Dagnaes-Hansen3, Robert A Fenton, Shan Gao, San Hein, Mingdong Dong, Jørgen Kjems and Kenneth A Howard. Protection and Systemic Translocation of siRNA Following Oral Administration of Chitosan/siRNA Nanoparticles. Molecular Therapy-Nucleic Acids (2013) 2, e76
31. Wilson, D S, Dalmasso, G, Wang, L, Sitaraman, S V, Merlin, D, Murthy, N. (2010). Orally delivered thioketal nanoparticles loaded with TNF-?-siRNA target inflammation and inhibit gene expression in the intestines. Nat Mater 9: 923-928.
32. Mohamed O. Elhassan, Jennifer Christie, and Mark S. Duxbury. Homo sapiens Systemic RNA Interference-defective-1 Transmembrane Family Member 1 (SIDT1) Protein Mediates Contact-dependent Small RNA Transfer and MicroRNA-21-driven Chemoresistance. THE JOURNAL OF BIOLOGICAL CHEMISTRY VOL. 287, NO. 8, pp. 5267-5277, Feb. 17, 2012
33. Mitchell P S, Parkin R K, Kroh E M, et al. Circulating microRNAs as stable blood-based markers for cancer detection. Proc Natl Acad Sci USA 2008; 105:10513-10518.
34. Xiang S, Fruehauf J, Li C J. Short hairpin RNA-expressing bacteria elicit RNA interference in mammals. Nat Biotechnol 2006; 24:697-702.
35. Kosaka N, Izumi H, Sekine K, et al. microRNA as a new immune-regulatory agent in breast milk. Silence 2010; 1:7.
36. Admyre C, Johansson S M, Qazi K R, et al. Exosomes with immune modulatory features are present in human breast milk. J Immunol 2007; 179:1969-1978
37. Wang K, Li H, Yuan Y, et al. The complex exogenous RNA spectra in human plasma: an interface with human gut biota? PLoS One 2012; 7:e51009
38. GaoFeng Liang1,2, YanLiang Zhu, Bo Sun, YouHua Shao, AiHua Jing, JunHua Wang & ZhongDang Xiao.

Assessing the survival of exogenous plant microRNA in mice. Food Science and Nutrition 2014
39. Schwarze, S. R. et al. (1999) In vivo protein transduction: delivery of a biologically active protein into the mouse. Science 285, 1569-1572
40. Herve Vaucheret. Plant ARGONAUTES. Trends in Plant Science Vol. 13 No. 7 2008
41. Kenneth W. Witwer. XenomiRs and miRNA homeostasis in health and disease. RNA Biology 9:9, 1147-1154; September 2012
42. Witwer K W, McAlexander M A, Queen S E, Adams R J. Real-time quantitative PCR and droplet digital PCR for plant miRNAs in mammalian blood provide little evidence for general uptake of dietary miRNAs: Limited evidence for general uptake of dietary plant xenomiRs. RNA Biology 2013; 10:1080-1086
43. Brent Dickinson, Yuanji Zhang, Jay S Petrick, Gregory Heck, Sergey Ivashuta & William S Marshall. Lack of detectable oral bioavailability of plant microRNAs after feeding in mice. Nature Biotechnology V31 N11 2013
43b. Xi Chen, Ke Zen and Chen-Yu Zhang reply. Nature Biotechnology V31 N11 2013
44. JUAN PABLO TOSAR, CARLOS ROVIRA, HUGO NAYA, and ALFONSO CAYOTA. Mining of public sequencing databases supports a non-dietary origin for putative foreign miRNAs:underestimated effects of contamination in NGS. RNA 20:1-4 2014
45. Marjorie Robbins, Adam Judge, Lisa Liang, Kevin McClintock, Ed Yaworski and Ian MacLachlan. 2'-O-methyl-modified RNAs Act as TLR7 Antagonists. Molecular Therapy (2007) 15 9, 1663-1669.
46. Aimee L. Jackson and Peter S. Linsley. Recognizing and avoiding siRNA off-target effects for target identification and therapeutic application. Nature Reviews Drug Discovery 9, 57-67 (January 2010)
47. Nick C. T. Schopman, Ying Poi Liu, Pavlina Konstantinova, Olivier ter Brake, Ben Berkhout. Optimization of shRNA inhibitors by variation of the terminal loop sequence. Antiviral Research 86 (2010) 204-211
48. Sayda M. Elbashir, Javier Martinez, Agnieszka Patkaniowska, Winfried Lendeckel and Thomas Tuschl. Functional anatomy of siRNAs for mediating efficient RNAi in *Drosophila melanogaster* embryo lysate. The EMBO Journal Vol. 20 No. 23 pp. 6877±6888, 2001
49. Marisa Colone, Massimo Tatti, MassimoIessi, Mariantonia Logozzi, Agnese Molinari, Angelo De Milito, Carolina Coscia, Elisabetta Raggi, Luana Lugini, Simonetta Palleschi, Isabella Parolini, Cristina Federici, Carla. Microenvironmental pH Is a Key Factor for Exosome Traffic in Tumor Cells. J. Biol. Chem. 2009, 284:34211-34222
50. Emily Anderson, Queta Boese, Anastasia Khvorova, and Jon Karpilow. Identifying siRNA-Induced Off-Targets by Microarray Analysis. Methods in Molecular Biology Volume 442, 2008, pp 45-63
51. Lawrence D. Joh, Tadeusz Wroblewski, Nicholas N. Ewing, Jean S. VanderGheynst. High-Level Transient Expression of Recombinant Protein in Lettuce. BIOTECHNOLOGY AND BIOENGINEERING, VOL. 91, NO. 7, Sep. 30, 2005
52. Flores-Jasso C F, Salomon W E, Zamore P D. Rapid and specific purification of Argonaute-small RNA complexes from crude cell lysates. RNA. 2013 February; 19(2):271-9
53. J Ma, C Dong and C Ji. MicroRNA and drug resistance. Cancer Gene Therapy (2010) 17, 523-531
54. Elina Zorde Khvalevskya, Racheli Gabaia, Itzhak Haim Rachmuta, Elad Horwitza, Zivia Brunschwiga, Ariel Orbacha, Adva Shemia, Talia Golanb, Abraham J. Dombc, Eylon Yavinc, Hilla Giladid, Ludmila Rivkind, Alina Simerzind, Rami Eliakime, Abed Khalailehf, Ayala Hubertg, Maor Lahave, Yael Kopelmanh, Eran Goldini, Alan Dancouri, Yael Hantsj, Sagit Arbel-Alonj, Rinat Abramovitchd, Amotz Shemia, and Eithan Galund. Mutant KRAS is a druggable target for pancreatic cancer. PNAS 2013 v110 n51

While certain of the preferred embodiments of the present invention have been described and specifically exemplified above, it is not intended that the invention be limited to such embodiments. Various modifications may be made thereto without departing from the scope of the present invention, as set forth in the following claims.

---

What is claimed is:

1. A plant cell transformed with a recombinant plant plastid or viral expression vector suitable for stable or transient plant transformation which comprises, as operably linked components in the 5' to 3' direction of translation, a promoter operable in said plant, a heterologous polynucleotide sequence coding for at least one RNAi molecule for downmodulation of Vac ATPase A gene expression and a transcription terminator functional in said plant, wherein said heterologous polynucleotide has high AT content and <60% GC content, and said RNAi molecule is optimized to comprise one or more stem loop structures while lacking complementarity to 3'UTRs in endogenous plant genes, said optimization reducing off target effects relative to RNAi molecules which are not optimized, said vector optionally encoding a nucleic acid encoding a selectable marker, said plant cell further comprising a heterologous polynucleotide sequence coding for an optimized RNAi that down-regulates a P450 monooxygenase gene expression in a second plastid transformation vector.

2. The vector of claim 1, wherein said one or both of said RNAi molecules has a 2 nucleotide TT 3' overhang.

3. The plant cell of claim 1, wherein said first or second vector further comprises a selectable marker which is an antibiotic resistance marker.

4. The plant cell of claim 1, further comprising a heterologous polynucleotide sequence coding for an optimized RNAi molecule that down-regulates a chitin synthase B gene in a third plastid transformation vector.

5. The plant cell of claim 1, which is present in an A edible transformed plant or portion thereof.

6. The plant portion as claimed in claim 5, wherein said portion is selected from the group consisting of seeds, leaves, flowers, roots and stems.

7. The plant cell in the transformed plant of claim 5 which is edible for mammals and humans.

8. The plant cell in the transformed plant of claim 5 which is a monocotyledonous or dicotyledonous plant.

9. The plant cell in the transformed plant of claim 5 which is maize, lettuce, rice, grass, rye, barley, oat, wheat, soybean, peanut, grape, potato, sweet potato, pea, canola, tobacco, tomato or cotton.

10. The transformed plant or plant portion of claim 5 which is lettuce.

11. The transformed plant of claim 5, wherein the plant comprises chloroplasts which are homoplasmic.

12. The transformed plant of claim 5, wherein the plant comprises chloroplasts which are heteroplasmic.

13. The plant cell of claim 4 present in an edible transformed plant or portion thereof.

* * * * *

SEQUENCE LISTING

```
<160> NUMBER OF SEQ ID NOS: 39

<210> SEQ ID NO 1
<211> LENGTH: 47
<212> TYPE: DNA
<213> ORGANISM: Artificial Sequence
<220> FEATURE:
<223> OTHER INFORMATION: Synthetic sequence

<400> SEQUENCE: 1
gcaacgaggt cgaaatgagt tcaagagact catttcgacc tcgttgc                47

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
aaaacccgtc tcagttcgg attgc                                         25
```

```
<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
ccgcgttgtt tcatcaagcc ttacg                                    25

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
ctgtagaagt caccattgtt gtgc                                     24

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
tgactgccca cctgagagcg gaca                                     24

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
agagactcat ttcgacctcg ttgct                                    25

<210> SEQ ID NO 7
<211> LENGTH: 26
<212> TYPE: DNA
<213> ORGANISM: Artificial Sequence
<220> FEATURE:
<223> OTHER INFORMATION: Primer

<400> SEQUENCE: 7
ggagcaatag caccctcttg atagaa                                   26

<210> SEQ ID NO 8
<211> LENGTH: 47
<212> TYPE: DNA
<213> ORGANISM: Artificial Sequence
<220> FEATURE:
<223> OTHER INFORMATION: Synthetic sequence

<400> SEQUENCE: 8
gtcactgacg tagtgctggt tcaagagacc agcactacgt cagtgac             47

<210> SEQ ID NO 9
<211> LENGTH: 47
<212> TYPE: DNA
<213> ORGANISM: Artificial Sequence
<220> FEATURE:
<223> OTHER INFORMATION: Synthetic sequence
```

<400> SEQUENCE: 9
ggtgaggacc gatggctctt tcaagagaag agccatcggt cctcacc         47

<210> SEQ ID NO 10
<211> LENGTH: 31
<212> TYPE: DNA
<213> ORGANISM: Artificial Sequence
<220> FEATURE:
<223> OTHER INFORMATION: Primer

<400> SEQUENCE: 10
ttccgtcgac gtagagaagt ccgtattttt c                          31

<210> SEQ ID NO 11
<211> LENGTH: 72
<212> TYPE: DNA
<213> ORGANISM: Artificial Sequence
<220> FEATURE:
<223> OTHER INFORMATION: Primer

<400> SEQUENCE: 11
gtcgaaatga gtctcttgaa ctcatttcga cctcgttgcc aacagtataa catgacttat    60
atactcgtgt ca                                                        72

<210> SEQ ID NO 12
<211> LENGTH: 74
<212> TYPE: DNA
<213> ORGANISM: Artificial Sequence
<220> FEATURE:
<223> OTHER INFORMATION: Primer

<400> SEQUENCE: 12
gacgtagtgc tggtctcttg aaccagcact acgtcagtga ccaacagtat aacatgactt    60
atatactcgt gtca                                                      74

<210> SEQ ID NO 13
<211> LENGTH: 72
<212> TYPE: DNA
<213> ORGANISM: Artificial Sequence
<220> FEATURE:
<223> OTHER INFORMATION: Primer

<400> SEQUENCE: 13
ccgatggctc ttctcttgaa agagccatcg gtcctcaccc aacagtataa catgacttat    60
atactcgtgt ca                                                        72

<210> SEQ ID NO 14
<211> LENGTH: 34
<212> TYPE: DNA
<213> ORGANISM: Artificial Sequence
<220> FEATURE:
<223> OTHER INFORMATION: Primer

<400> SEQUENCE: 14
cagttgacct gcagcccaaa caaatacaaa atca                       34

<210> SEQ ID NO 15
<211> LENGTH: 58
<212> TYPE: DNA
<213> ORGANISM: Artificial Sequence
<220> FEATURE:
<223> OTHER INFORMATION: Primer

<400> SEQUENCE: 15

```
tgagttcaag agactcattt cgacctcgtt gctttttttc tagagatcct ggcctagt        58
```

<210> SEQ ID NO 16
<211> LENGTH: 57
<212> TYPE: DNA
<213> ORGANISM: Artificial Sequence
<220> FEATURE:
<223> OTHER INFORMATION: Primer

<400> SEQUENCE: 16

```
tggttcaaga gaccagcact acgtcagtga cttttttct agagatcctg gcctagt         57
```

<210> SEQ ID NO 17
<211> LENGTH: 57
<212> TYPE: DNA
<213> ORGANISM: Artificial Sequence
<220> FEATURE:
<223> OTHER INFORMATION: Primer

<400> SEQUENCE: 17

```
tctttcaaga gaagagccat cggtcctcac ctttttttct agagatcctg gcctagt        57
```

<210> SEQ ID NO 18
<211> LENGTH: 11
<212> TYPE: RNA
<213> ORGANISM: Artificial Sequence
<220> FEATURE:
<223> OTHER INFORMATION: Synthetic sequence

<400> SEQUENCE: 18

```
ugauaugugc a                                                          11
```

<210> SEQ ID NO 19
<211> LENGTH: 14
<212> TYPE: RNA
<213> ORGANISM: Artificial Sequence
<220> FEATURE:
<223> OTHER INFORMATION: Synthetic sequence

<400> SEQUENCE: 19

```
ccucucaaca cugg                                                       14
```

<210> SEQ ID NO 20
<211> LENGTH: 19
<212> TYPE: RNA
<213> ORGANISM: Artificial Sequence
<220> FEATURE:
<223> OTHER INFORMATION: Synthetic sequence

<400> SEQUENCE: 20

```
gcgugugcug ucccguugc                                                  19
```

<210> SEQ ID NO 21
<211> LENGTH: 794
<212> TYPE: DNA
<213> ORGANISM: Artificial Sequence
<220> FEATURE:
<223> OTHER INFORMATION: Synthetic sequence

<400> SEQUENCE: 21

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
```

```
ctcgtgacca ccctgaccta cggcgtgcag tgcttcagcc gctaccccga ccacatgaag        240
gcacgacttc ttcaagtccg ccatgcccga aggctacgtc caggagcgca ccatcttctt        300
caaggacgac ggcaactaca agacccgcgc cgaggtgaag ttcgagggcg acaccctggt        360
gaaccgcatc gagctgaagg gcatcgactt caaggaggac ggcaacatcc tggggcacaa        420
gcgagtacaa ctacaacagc cacaacgtct atatcatggc cgacaagcag aagaacggca        480
tcaaggtgaa cttcaagatc cgccacaaca tcgaggacgg cagcgtgcag ctcgccgacc        540
actaccagca gaacaccccc atcggcgacg gccccgtgct gctgcccgac aaccactacc        600
tgagcaccca gtccgccctg agcaaagacc ccaacgagaa gcgcgatcac atggtcctgc        660
tggagttcgt gaccgccgcc gggatcactc tcggcatgga cgagctgtac aagtccggac        720
tcagatctcg agctcaagct tcgaattctg cagtcgacgg taccgcgggc ccgggatcca        780
ccggatctag ataa                                                          794
```

```
<210> SEQ ID NO 22
<211> LENGTH: 21
<212> TYPE: DNA
<213> ORGANISM: Artificial Sequence
<220> FEATURE:
<223> OTHER INFORMATION: Synthetic sequence

<400> SEQUENCE: 22
aagcagcacg acttcttcaa g                                                   21

<210> SEQ ID NO 23
<211> LENGTH: 21
<212> TYPE: DNA
<213> ORGANISM: Artificial Sequence
<220> FEATURE:
<223> OTHER INFORMATION: Synthetic sequence

<400> SEQUENCE: 23
aagctggagt acaactacaa c                                                   21

<210> SEQ ID NO 24
<211> LENGTH: 47
<212> TYPE: DNA
<213> ORGANISM: Artificial Sequence
<220> FEATURE:
<223> OTHER INFORMATION: shRNA

<400> SEQUENCE: 24
gctacgtcca ggagcgcacc ctcgagggtg cgctcctgga cgtagcc                       47

<210> SEQ ID NO 25
<211> LENGTH: 50
<212> TYPE: DNA
<213> ORGANISM: Artificial Sequence
<220> FEATURE:
<223> OTHER INFORMATION: shRNA

<400> SEQUENCE: 25
gctacgtcca ggagcgcacc accaagaagg gtgcgctcct ggacgtagcc                    50

<210> SEQ ID NO 26
<211> LENGTH: 51
<212> TYPE: DNA
<213> ORGANISM: Artificial Sequence
<220> FEATURE:
<223> OTHER INFORMATION: shRNA

<400> SEQUENCE: 26
```
gctacgtcca ggagcgcacc accaagaagg gtgcgctcct ggacgtagct t        51

<210> SEQ ID NO 27
<211> LENGTH: 59
<212> TYPE: DNA
<213> ORGANISM: Artificial Sequence
<220> FEATURE:
<223> OTHER INFORMATION: Synthetic Sequence

<400> SEQUENCE: 27
gatcgcagca cgacttcttc aagaccaaga agcttgaaga agtcgtgctg ctttttttt        59

<210> SEQ ID NO 28
<211> LENGTH: 59
<212> TYPE: DNA
<213> ORGANISM: Artificial Sequence
<220> FEATURE:
<223> OTHER INFORMATION: Synthetic Sequence

<400> SEQUENCE: 28
tcgaaaaaaa aagcagcacg acttcttcaa gcttcttggt cttgaagaag tcgtgctgc        59

<210> SEQ ID NO 29
<211> LENGTH: 59
<212> TYPE: DNA
<213> ORGANISM: Artificial Sequence
<220> FEATURE:
<223> OTHER INFORMATION: Synthetic Sequence

<400> SEQUENCE: 29
gatcgcagca cgacttcttc aagaccaaga agcttgaaga agtcgtgctg cttactagt        59

<210> SEQ ID NO 30
<211> LENGTH: 59
<212> TYPE: DNA
<213> ORGANISM: Artificial Sequence
<220> FEATURE:
<223> OTHER INFORMATION: Synthetic sequence

<400> SEQUENCE: 30
tcgaactagt aagcagcacg acttcttcaa gcttcttggt cttgaagaag tcgtgctgc        59

<210> SEQ ID NO 31
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 31
accatcttct tcaaggacga c        21

<210> SEQ ID NO 32
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 32
gtcgtccttg aagaagatgg t        21

<210> SEQ ID NO 33
<211> LENGTH: 50
<212> TYPE: DNA

<213> ORGANISM: Artificial Sequence
<220> FEATURE:
<223> OTHER INFORMATION: Synthetic Sequence

<400> SEQUENCE: 33

| gcctgggacg tgacctatgc tgaggtattc gcactggata cgacaccatc | 50 |
|---|---|

<210> SEQ ID NO 34
<211> LENGTH: 19
<212> TYPE: DNA
<213> ORGANISM: Artificial Sequence
<220> FEATURE:
<223> OTHER INFORMATION: Primer

<400> SEQUENCE: 34

| caacgcagtc gtccttgaa | 19 |
|---|---|

<210> SEQ ID NO 35
<211> LENGTH: 122
<212> TYPE: RNA
<213> ORGANISM: Artificial Sequence
<220> FEATURE:
<223> OTHER INFORMATION: shRNA

<400> SEQUENCE: 35

| caagagaaac gcaaagaaac ugacagaaga gagugagcac acaaaggcaa uuugcauauc | 60 |
|---|---|
| auugcacuug cuucucuugc gugcucacug cucuuucugu cagauuccgg ugcugaucuc | 120 |
| uu | 122 |

<210> SEQ ID NO 36
<211> LENGTH: 49
<212> TYPE: DNA
<213> ORGANISM: Artificial Sequence
<220> FEATURE:
<223> OTHER INFORMATION: shRNA

<400> SEQUENCE: 36

| gcagcacgac ttcttcaaga ccaagaagct tgaagaagtc gtgctgctt | 49 |
|---|---|

<210> SEQ ID NO 37
<211> LENGTH: 49
<212> TYPE: DNA
<213> ORGANISM: Artificial Sequence
<220> FEATURE:
<223> OTHER INFORMATION: shRNA

<400> SEQUENCE: 37

| gctggagtac aactacaaca ccaagaaggt tgtagttgta ctccagctt | 49 |
|---|---|

<210> SEQ ID NO 38
<211> LENGTH: 830
<212> TYPE: DNA
<213> ORGANISM: Artificial Sequence
<220> FEATURE:
<223> OTHER INFORMATION: Kras G12D2 vector sequence

<400> SEQUENCE: 38

| asccyttcwt cgcttcttgm gagttcttct gagcgggact ctggggttcg gactctagct | 60 |
|---|---|
| agaggatcaa ttcggtacgc tgaaatcacc agtctctctc tacaaatcta tctctctcta | 120 |
| ttttctccat aaataatgtg tgagtagttt cccgataagg gaaattaggg ttcttatagg | 180 |
| gtttcgctca tgtgttgagc atataagaaa cccttagtat gtatttgtat ttgtaaaata | 240 |
| cttctatcaa taaatttct aattcctaaa accaaaatcc agtactaaaa tccagatcga | 300 |

```
tccaccgcgg aactcgactt gccttccgca caatacatca tttcttctta gctttttttc    360
ttcttcttcg ttcatacagt ttttttttgt ttatcagctt acattttctt gaaccgtagc    420
tttcgttttc ttcttttaa ctttccattc ggagttttg tatcttgttt catagtttgt    480
cccaggatta gaatgattag gcatcgaacc ttcaagaatt tgattgaata aaacatcttc    540
attcttaaga tatgaagata atcttcaaaa ggcccctggg aatctgaaag aagagaagca    600
ggcccattta tatgggaaag aacaatagta tttcttatat aggcccattt aagttgaaaa    660
caatcttcaa aagtcccaca tcgcttagat aagaaaacga agctgagttt atatacagct    720
agagtcgaag tagtgattgt cccttcgggg acatccgata aattggaaty sgttggagct    780
gatggcgtag accaagaagc tacgccatca gctccaactt tttttttcgac    830
```

```
<210> SEQ ID NO 39
<211> LENGTH: 908
<212> TYPE: DNA
<213> ORGANISM: Artificial Sequence
<220> FEATURE:
<223> OTHER INFORMATION: Kras3 vector sequence

<400> SEQUENCE: 39
ascccatcwt cgccttcttg acgagttctt ctgagcggga ctctggggtt cggactctag    60
ctagaggatc ataagttacg ctgaaatcac cagtctctct ctacaaatct atctctctct   120
attttctcca taaataatgt gtgagtagtt tcccgataag ggaaattagg gttcttatag   180
ggtttcgctc atgtgttgag catataagaa acccttagta tgtatttgta tttgtaaaat   240
acttctatca ataaaatttc taattcctaa aaccaaaatc cagtactaaa atccagatcg   300
atccaccgcg gaactcgact tgccttccgc acaatacatc atttcttctt agctttttt    360 cttcttcttc gttcatacag tttttttttg tttatcagct tacattttct tgaaccgtag    420
ctttcgtttt cttcttttta actttccatt cggagttttt gtatcttgtt tcatagtttg    480
tcccaggatt agaatgatta ggcatcgaac cttcaagaat ttgattgaat aaaacatctt    540
cattcttaag atatgaagat aatcttcaaa aggcccctgg gaatctgaaa gaagagaagc    600
aggcccattt atatgggaaa gaacaatagt atttcttata taggcccatt taagttgaaa    660
acaatcttca aaagtcccac atcgcttaga taagaaaacg aagctgagtt tatatacagc    720
tagagtcgaa gtagtgattg tcccttcggg gacatccgat aaaattggat ysgttggrrg    780
ctggtggcgt agcttcttgg tctacgccac cagctccaac ttttttttcg acgtccgcaa    840
aaatcaccag tctctctcta caaatctatc tctctctatt tttctccarr aataatgktg    900 tgragtag                                                              908
```